US006100451A

United States Patent [19]
Chappell et al.

[11] Patent Number: 6,100,451
[45] Date of Patent: Aug. 8, 2000

[54] PATHOGEN-INDUCIBLE REGULATORY ELEMENT

[75] Inventors: Joseph Chappell; Catherine A. G. Cornett; Shauhui Yin, all of Lexington, Ky.

[73] Assignee: Board of Trustees of the University of Kentucky, Lexington, Ky.

[21] Appl. No.: 08/577,483

[22] Filed: Dec. 22, 1995

Related U.S. Application Data

[63] Continuation-in-part of application No. 08/471,983, Jun. 6, 1995, abandoned, which is a continuation of application No. 08/443,639, May 18, 1995.

[51] Int. Cl.[7] .............................. A01H 5/00; A01H 5/10; C07H 21/04; C12N 5/14; C12N 15/82
[52] U.S. Cl. ..................... 800/298; 435/320.1; 435/419; 435/468; 536/24.1; 800/278; 800/279; 800/298; 800/301; 800/317; 800/317.3; 800/319
[58] Field of Search ........................ 536/24.1; 435/320.1, 435/172.3, 240.4, 419; 800/205, 250, 255, DIG. 43, DIG. 9, DIG. 40, DIG. 52

[56] References Cited

FOREIGN PATENT DOCUMENTS

| 0332104 | 9/1989 | European Pat. Off. . |
|---|---|---|
| 0392225 | 10/1990 | European Pat. Off. . |
| WO 90/05187 | 5/1990 | WIPO . |
| WO 93/19188 | 9/1993 | WIPO . |

OTHER PUBLICATIONS

Bonnet et al., J. Phytopathology 141:25–37, 1994.
Colby et al., J. Biol. Chem. 268:23016–23024, 1993.
Hohn et al., Plant Physiol. 97:490–462, 1991.
Wehner et al., Mol. Gen. Genet. 237:351–358, 1993.
Albersheim and Valent, J. Cell. Biol. 78:627–643, 1978.
Back et al., Arch. Biochem. Biophys. 315:527–532, 1994.
Blein et al., Plant Physiol. 95:486–491, 1991.
Chappell et al., Plant Physiol. 97:693–698, 1991.
Facchini and Chappell, Proc. Natl. Acad. Sci. USA 89:11088–11092, 1992.
Guedes et al., Phytochemistry 21:2987–2988, 1982.
Hammond–Kosack et al., Proc. Natl. Acad. Sci. USA 91:10445–10449, 1994.
Huet and Pernollet, FEBS Lett. 257:302–306, 1989.
Huet et al., Phytochemistry 31:1471–1476, 1992.
Kamoun et al., Mol. Plant–Microbe Interact. 5:22–33, 1992.
Kamoun et al., Mol. Plant–Microbe Interactions 6:573–581, 1993.
Milat et al., Phytochemistry 30:2171–2173, 1991.
Nespoulous et al., Planta 186:551–557, 1992.
Newman et al., Plant Physiol., 108:Abstract #575, 1995.
Ricci et al., Eur. J. Biochem. 183:555–563, 1989.
Saiki et al., Science 239:487–491, 1988.
Sequeira, Annu. Rev. Microbiol. 37:51–79, 1983.
Tedford et al., Plant Disease 74:313–316, 1990.
Vogeli and Chappell, Plant Physiol. 94:1860–1866, 1990.
Vogeli et al., Plant Physiol. 93:182–187, 1990.
Yin et al., Plant Physiol. 108:Abstract #574, 1995.
Yu, Proc. Natl. Acad. Sci. USA 92:4088–4094, 1995.
Zhu et al., The Plant Journal 7:1021–1030, 1995.
Gough et al., "Developmental and Pathogen–induced Activation of an msr Gene, str 246C, from Tobacco Involves Multiple Regulatory Elements", Mol. Gen. Genet 247:323–337, 1995.
Huang et al., "Bacterial Induced Activation of an Arabidopsis Phenylalanine Ammonia–lyase Promoter in Transgenic Tobacco Plants", Plant Science 98:25–35, 1994.
Wehner, et al (1993) Mol. Gen. Genet. 237: 351–358.
Bonnet, et al. (1994) J. Phytopathology 141: 25–37.
Kamoun, et al. (1993) Molecular Plant–Microbe Interactions 6(5): 573–581.
Samac, et al (Oct. 10, 1991) The Plant Cell vol. 3: 1063–1072.
Van de Rhee, et al. (Apr. 1990) The Plant Cell 2: 357–366.
Meier, et al. (Mar. 1991) The Plant Cell 3: 309–315.
Gough, et al. (1995) Mol. Gen. Genet. 247: 323–337.
Huang, et al. (1994) Plant Science 98: 25–35.

*Primary Examiner*—Douglas W. Robinson
*Assistant Examiner*—Amy J. Nelson
*Attorney, Agent, or Firm*—Clark & Elbing LLP

[57] ABSTRACT

Qualitative transcriptional regulatory sequences functional in plants, plant tissue and in plant cells for inducible gene expression and quantitative transcriptional regulatory sequences for increasing the transcriptional expression of downstream genetic information in plants, plant tissue and plant cells are disclosed. Also disclosed are methods and recombinant DNA molecules for improving the disease resistance of transgenic plants, especially wherein an inducible promoter controls the expression of a protein capable of evoking the hypersensitive response in a plant.

54 Claims, 12 Drawing Sheets

-1148
AAGCTTTACGAATTAGATGTAAAAGACACAAACTACTTATATATATTAC
CAAAGTAACTTGAAAGTTTAAAATTTCAATTAGAACTATAGTAGGGTAAA
ACTGTCTATTTAAAATCAGTATTTAAAAAGGCATGAGCGAAAGATGAGGC
GTTTTATCTAACACGAAGCGAGGTGTAAGCCCCATGGTGTTTTATTTTTA
TATTTTATAAATTTATAAAATCATTATATAAATCAGAAAAATACACTAAA
ATTGTGAAAGTTAAAGAAAATTATAGAATTAATATATATATATATATAT
ATATATATATATATATATATATATATATATATATATAAATGTATGTGT
GTGTGTGTGTATCGCATGCGCGCGACCATGCAACTTTTTTTTCTTGAA
AAAATAAAAGGCGTAAAGATACATTATACCTATGTCATCAAAACAATATA
AAAACTAGAGCGATACCAAAGGAAATTTTAAATTCAAAAACTAACTTGAA
ATTAATATATTTAAAATTTCATTTTTTTTTGTGTGGAGAAAACAAAGCAT
AACACTTTGCTTTGTAACACTTTGCCTAGGTGAATGTCAGGGCTTATGCT
CCACGATACTTATGCCCTGCCAGTACACCTCGCAGTGGGACTCGCTGAAA
AAACGTCTTTGTTGTGAGAAATTGCAATTTTGAACCTCTACAATTTCGAC
AAAACCTTGGTTCGTGAAAACTGTTTGATTAACTTTTAGACCATCCAGTC
AATTTAACTCTAAACTGACCTAAATAAATACTACGTACACTAGTCTTTAA
GTTCATCAAAGTGGACTCTGCATTAATAATTGAAATTTATGCCGCAACAA
TGACATTAGGTTTTATAAATAAAGTAATAGGAATTTGATAGTTCCAGGAA
ACAACTCTACAGTACTCCCTTATTTTGTGCCTTTTTAAATAATATTATTC
AGTTGACGAAACAAATAAATAAAATATTTGGGAAACTGGATCAATAGACC
CCAGACGCCAACAATGAATCAAAAGGCTGCTAGCTAGTGTAAAGTCTAGT
AAGGCAACTGGGAAATTAAATGATTAGGTGCTTTTGATCAATTACATTAA
CTAGTCTCTCACCACTATATATACTTGTCCCTTCTCTTCCATTTAAGTA$^{+1}$G
AGTTCCTTTCTTTCTTCCTTAAAACTTAAAAGAACAAGTAAAAATACACT
CATCTTTAATTAGCA
+67

FIG. 3A

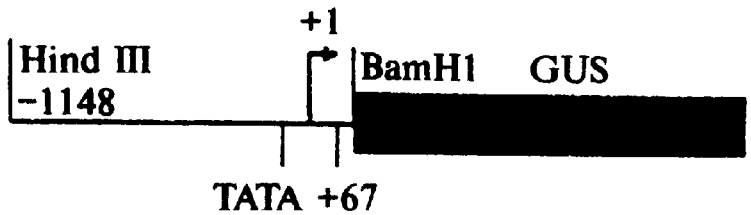

FIG. 3B

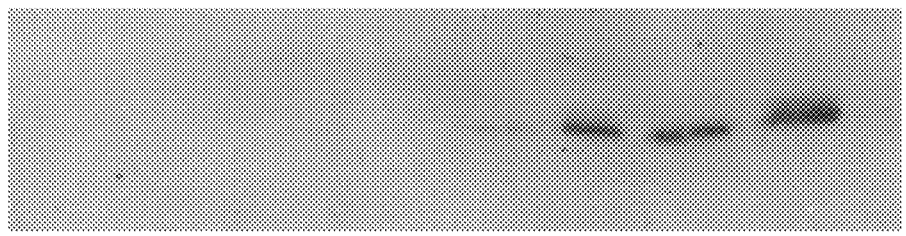
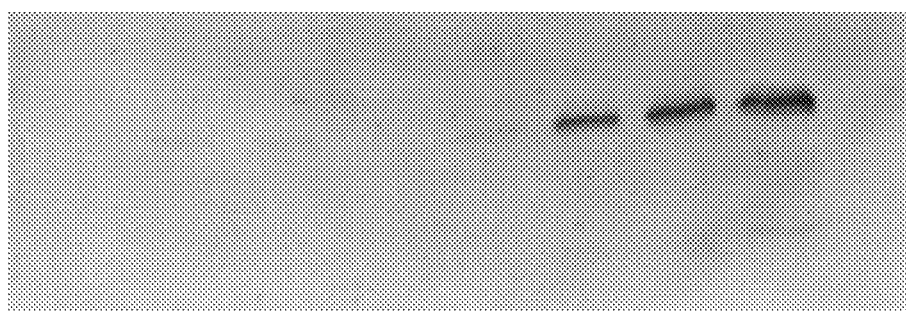
FIG. 7A
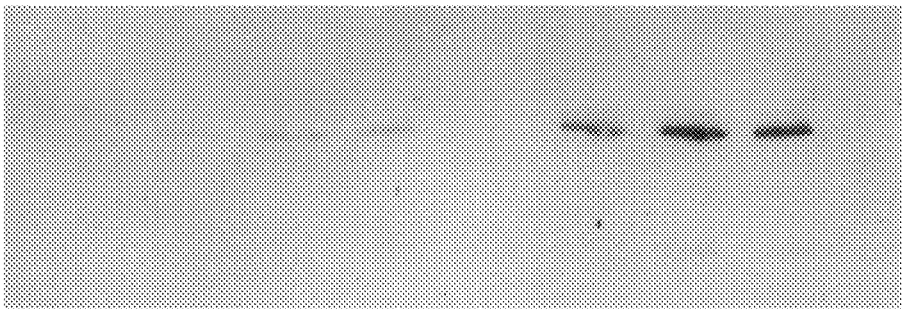
FIG. 7B

PATHOGEN-INDUCIBLE REGULATORY ELEMENT

CROSS REFERENCE TO RELATED APPLICATIONS

This application is a continuation-in-part of Ser. No. 08/471,983 filed on Jun. 6, 1995, now abandoned, which is a continuation of Ser. No. 08/443,639, which was filed on May 18, 1995, the disclosures of which are hereby incorporated by reference.

STATEMENT AS TO FEDERALLY SPONSORED RESEARCH

This invention was made, at least in part, with funding from the National Science Foundation and the United States Department of Agriculture. Accordingly, the United States Government may have certain rights in this invention.

1. The Field of the Invention

The field of this invention is the area of plant molecular biology, and it relates in particular to transcription regulatory elements: a qualitative regulatory sequence which positively regulates downstream gene expression in plant tissue in response to the stress of an invading microbial pathogen, an elicitor, or other inducing chemical signals and quantitative regulatory sequences which increase the transcriptional expression of associated sequences.

2. The Background of the Invention

In plants, disease resistance to fungal, bacterial, and viral pathogens is associated with a plant response termed the hypersensitivity response (HR). In the HR, the site in the plant where the potential phytopathogen invades undergoes localized cell death, and it is postulated that this localized plant cell death aspect of the HR contains the invading microorganism or virus, thereby protecting the remainder of the plant. Other plant defenses include the production of phytoalexins (antibiotics) and/or lytic enzymes capable of averting pathogen ingress and/or cell wall modifications which strengthen the plant cell wall against physical and/or enzymatic attack.

The HR of plants, including tobacco, can include phytoalexin production as part of the response to invading microorganisms. One class of compounds made by tobacco (*Nicotiana tabacum*) in response to microbial invaders are the antimicrobial sesquiterpenes.

Cell suspension cultures have provided useful information regarding the regulation of terpene synthesis. Isoprenoids are ubiquitous in nature, and the early portions of the biosynthetic pathway are shared with the biosynthetic pathway for other isoprenoid compounds such as sterols, carotenoids, dolichol, and ubiguinone and growth regulators (e.g., gibberellic acid), which are classified as primary metabolites. Isoprenoid compounds classified as secondary metabolites are not essential for growth, and include mono-, sesqui-, and diterpenoids. These secondary metabolite isoprenoids are important mediators of interactions between the plant and its environment.

A variety of compositions can serve as elicitors of plant phytoalexin synthesis. These include, but are not limited to, one or more toxic ions, e.g., mercuric ions, other chemically defined compositions, metabolic inhibitors, cell wall glycans, certain glycoproteins, certain enzymes, fungal spores, chitosans, certain fatty acids, and certain oligosaccharides derived from plant cell walls [See, e.g., Sequeira, L. (1983) *Annu. Rev. Microbiol.* 37:51–79 and references cited therein]. Epi-5-aristolochene synthase (EAS) activity in tobacco plants has been shown to be induced by cell wall fragments of certain Phytophthora species and by *Trichoderma viride* cellulase but not *Aspergillus japonicum* pectolyase [Chappell et al. (1991) *Plant Physiol.* 97:693–698]. Attack by other plant pathogens or an avirulent related strain can also induce phytoalexin synthesis; for example, *Pseudomonas lachrymans* induces sesquiterpenoid synthesis in tobacco [Guedes et al. (1982) *Phytochemistry* 21:2987–2988].

Elicitins are proteins which are produced by plant pathogens and potential plant pathogens, which proteins induce the HR in tobacco plants. Amino acid and nucleotide coding sequences for an elicitin of *Phytophthora parasitica* have been published [Kamoun et al. (1993) *Mol. Plant-Microbe Interactions* 6:573–581]. Plant pathogenic viruses including, but not limited to, Tobacco Mosaic Virus (TMV) induce the HR in infected plants. Bacteria which infect plants also can induce HR and thereby disease resistance; representative bacteria eliciting HR include, but are not limited to, Agrobacterium species, Xanthomonas species and *Pseudomonas syringae*. Plant pathogenic fungi (and certain avirulent strains as well) also induce the HR response, where these include, but are not limited to, *Phytophthora parasitica* and *Peronospora tabaci*.

When tobacco cell suspension cultures are treated with an elicitor, squalene synthetase is suppressed, thus stopping the flow of common biosynthetic precursors into sterols. The concomitant induction of sesquiterpene cyclase gene expression causes the flow of precursors into sesquiterpenes. The first step in the pathway from farnesyl diphosphate to the sesquiterpene phytoalexin capsidiol in elicitor-induced tobacco tissue is catalyzed by 5-epi-aristolochene synthase (EAS), a sesquiterpene cyclase. The coding sequence and deduced amino acid sequence for one member of the EAS gene family of tobacco have been published [Facchini and Chappell (1992) *Proc. Natl. Acad. Sci. USA* 89:11088–11092]. The transcriptional expression of one or more members of the EAS gene family is induced in response to elicitors.

There is a long felt need in the art for methods of protecting plants, particularly crop plants, from infection by plant pathogens, including but not limited to, phytopathogenic viruses, fungi and/or bacteria. Especially important from the standpoint of economics and environmental concerns are biological or "natural" methods rather than those which depend on the application of chemicals to crop plants. There is also a long felt need in the art for plant transcriptional regulatory sequences for use in controlling the expression of heterologous DNA sequences in transgenic plants.

SUMMARY OF THE INVENTION

In general, the invention features a recombinant nucleic acid molecule that includes an inducible plant disease-resistance regulatory element. Such a recombinant nucleic acid molecule is, in general, at least 80% identical to a naturally-occurring inducible plant disease-resistance regulatory element; that is, up to 20% of the base pairs of the reference DNA sequence can be replaced with an alternative basepair (e.g., G-C replaced with A-T, T-A, or C-G), provided that the transcription-promoting activity of the altered sequence is the same or greater than the reference sequence. In preferred embodiments, the recombinant nucleic acid molecule according to the invention is obtained from a gene encoding a terpene cyclase (e.g., a sesquiterpene cyclase). For example, the recombinant regulatory element of the invention is obtained from an epi-5-aristolochene synthase (EAS) gene that includes the nucleotide sequence shown in FIG. 3A (SEQ ID NO: 14) or an inducible plant disease-resistance fragment thereof. In preferred embodiments, the recombinant nucleic acid molecule according to the invention has the nucleotide sequence shown in FIG. 3A (SEQ ID NO: 14).

In other preferred embodiments, the nucleic acid molecules of the invention includes any of the following sequences: nucleotides 463–473 of SEQ ID NO: 2; nucleotides 406–486 of SEQ ID NO: 2; nucleotides 463–572 of SEQ ID NO: 2; nucleotides 371–463 of SEQ ID NO: 2; and nucleotides 411–457 of SEQ ID NO: 2.

In preferred embodiments, the recombinant nucleic acid molecule of the invention is obtained from a dicot (e.g., a member of the Solanaceae such as Nicotiana). In other preferred embodiments, the nucleic acid of the invention is obtained from a monocot; a gymnosperm; or a conifer.

In yet other preferred embodiments, the nucleic acid molecule of the invention is genomic DNA; chemically-synthesized DNA; or is a combination of genomic DNA and chemically-synthesized DNA; genomic DNA and cDNA; chemically-synthesized DNA and cDNA; or genomic DNA, cDNA, and chemically-synthesized DNA.

In preferred embodiments, induction of the nucleic acid molecule of the invention is mediated by a plant pathogen such as a fungus (e.g., Phytophthora), a bacterium (e.g., Pseudomonas), or a virus (e.g., tobacco mosaic virus) as described herein. In other preferred embodiments, such induction is mediated by an elicitor (e.g., by fungal or bacterial elicitors).

In another aspect, the nucleic acid molecule of invention is operably linked to and functions to regulate inducible transcription of nucleotide sequences encoding a heterologous polypeptide. Preferably, the heterologous polypeptide is capable of conferring disease-resistance to a plant. For example, the heterologous polypeptide may be an elicitin (e.g., a fungal elicitin such as the parAl polypeptide from Phytophthora, a bacterial elicitin such as harpin, or a pharmaceutical polypeptide such as tissue plasminogen activator). Expression of such a heterologous polypeptide is mediated by one or more external agents (e.g., ethylene or methyl jasmonate). In other embodiments, the nucleic acid molecule of invention is capable of expressing the heterologous polypeptide in a cell-specific manner.

In another aspect, the invention features a vector including the nucleic acid molecule of the invention, a method of directing expression of a polypeptide by introducing the vector into a cell (e.g., a transgenic plant cell), and a cell containing the vector.

In another aspect, the invention features a method of providing disease-resistance to a transgenic plant, the method including the steps of: (a) producing a transgenic plant cell including the nucleic acid of according to the invention integrated into the genome of the transgenic plant cell; and (b) growing the transgenic plant from the plant cell wherein the expression of the nucleic acid molecule according to the invention confers disease-resistance to the transgenic plant.

In preferred embodiments, the transgenic plant according to the methods of the invention is a dicot (e.g., is a member of the Solanaceae such as Nicotiana); a monocot; a gymnosperm; or a conifer.

In another aspect, the invention features a method of increasing the transcriptional expression of a downstream DNA sequence in a transgenic plant cell, the method including the steps of: (a) producing a transgenic plant cell including the nucleic acid of invention positioned for increasing transcription of a downstream DNA sequence and integrated into the genome of the transgenic plant cell; and (b) growing the transgenic plant from the plant cell.

In addition to the above features, the present invention provides qualitative transcriptional regulatory sequences which regulate downstream gene expression in plant tissue in response to one or more elicitors, other defined inducing compounds, or in response to the stress of an invading phytopathogen (the inducible transcription regulatory sequence) and quantitative transcription regulatory sequences which increase the transcription of downstream sequences (the transcription-enhancing sequence). As specifically exemplified herein, these transcriptional regulatory sequences are found in nature upstream and operatively linked to the epi-5-aristolochene synthase gene (EAS4) of tobacco; when operatively linked to a coding sequence (and in the presence of an operatively linked promoter element, from the EAS4 gene or from a heterologous plant-expressible gene) these sequences mediate the inducible transcriptional expression of that coding sequence when the plant or plant tissue is invaded by a potential phytopathogen (e.g., a virus, fungus or bacterium) or in response to elicitors such as *Trichoderma viride* cellulase or plant or fungal cell wall fragments for plants, plant tissue and/or plant suspension culture cells. That potential plant pathogen can be a virus including, but not limited to, tobacco mosaic virus or tobacco vein mottle virus; a bacterium including, but not limited to, *Pseudomonas syringae, Xanthomonas campestris* or *Agrobacterium tumefaciens*; or a fungus including, but not limited to, a species of Phytophthora (e.g., *P. parasitica*) or Peronospora (e.g., *P. tabaci*). The EAS4 promoter including the inducible transcription regulatory element(s) and the transcription-enhancing sequence(s) are disclosed herein as SEQ ID NO:2. In SEQ ID NO:2, the CAAT-homologous sequence of the EAS4 promoter is located at nucleotides 513 to 516, and the TATA-sequence motif is located at nucleotides 540 to 543.

Examples of inducible transcriptional regulatory elements within the *N. tabacum* EAS4 upstream sequence are from nucleotide 458 to nucleotide 473 of SEQ ID NO:2; from nucleotide 454 to 473; and from nucleotide 413 to 473 of SEQ ID NO:2.

Another aspect of the present invention is the transcription-enhancing element derived from the EAS4 promoter and promoter-associated sequences. When operatively linked upstream of a initiation sequences and a heterologous DNA sequence to be expressed.

Further aspects of the present invention are transgenic plant cells, plant tissues, and plants which have been genetically engineered to contain and express a nucleotide sequence of interest, preferably a coding sequence, an antisense sequence, or other sequence under the regulatory control of the inducible transcription regulatory element. It is an object of this invention to provide the nucleotide sequences which mediate the induction of the expression of a downstream coding sequence in response to elicitor exposure, potential phytopathogen invasion in a plant, or certain other exogenous inducing signals such as exposure to methyl jasmonate and ethylene. An exemplary elicitor inducible transcription regulatory element is that from the 5' flanking region of the EAS4 gene of *Nicotiana tabacum*; as specifically exemplified herein, this sequence is presented in SEQ ID NO:2 from nucleotide 410 to nucleotide 473. Equivalents of the exemplified nucleotide sequence are those nucleotide sequences which similarly direct the induction of the expression of downstream nucleotide sequences.

Preferably, the inducible transcription regulatory element is associated with the EAS4 promoter and promoter-associated sequences (e.g., the combination having the nucleotide sequence as given in SEQ ID NO:2 from nucleotide 410 to nucleotide 573 of SEQ ID NO:2, preferably from nucleotide 361 to 573 of SEQ ID NO:2, and more preferably from nucleotide 1 to 573 of SEQ ID NO:2).

By "disease-resistance regulatory element" is meant a DNA sequence capable of regulating the expression of a gene product associated with a plant defense response (e.g., a hypersensitive response) that, in a native plant, is used to a combat pathogenic organism. Also included in this term are regulatory elements (and, as defined below, fragments of such regulatory elements) that are sufficient to render gene expression inducible by disease-associated external signals or agents (e.g., pathogen- or elicitor-induced signals or agents as described herein). In general, disease-resistance regulatory elements are located in the 5' region of a gene, but are not so limited.

By "inducible" is meant that a regulatory element is capable of mediating increased gene expression (e.g., mRNA or polypeptide production) in response to an interaction between a plant cell and either a pathogen or elicitor. Also included in the invention are disease-resistance regulatory elements that direct inducible gene expression in a cell- or tissue-specific manner.

By "obtained from a gene" is meant that the nucleotide sequence of a regulatory element is based on sequence information included in a naturally-occurring plant gene (e.g., tobacco EAS4). Once identified, the regulatory element according to the invention is obtained from a natural source or can be prepared according to any standard method (e.g., by recombinant methods or chemical synthesis). Such a recombinant nucleic acid molecule is, in general, at least 80% identical to a naturally-occurring inducible plant disease-resistance regulatory element; that is, up to 20% of the base pairs of the reference DNA sequence can be replaced with an alternative basepair (e.g., G-C replaced with A-T, T-A, or C-G), provided that the transcription-promoting activity of the altered sequence is the same or greater than the reference sequence.

By "an inducible plant disease-resistance fragment" is meant any stretch of nucleotides regardless of length, which is sufficient to direct increased gene expression (e.g., mRNA or polypeptide production) in response to an interaction between a plant cell and either a pathogen or elicitor. The term "fragment" preferably means about 6–10 nucleotides in length. However, fragments of DNA regulatory elements according to the invention can range in size from 10–100 nucleotides, 100–300 nucleotides in length, or even greater than 300 nucleotides in length. Such fragments are prepared by routine methods (e.g., by appropriate restriction digestion or by chemical synthesis of the fragment). Identification of an inducible plant disease-resistance DNA fragment in a gene is carried out using standard methods in the art (e.g., those methods described herein). In one particular example, identification of an inducible plant disease-resistance fragment may be carried out using standard promoter deletion analysis. A construct including a disease-resistance promoter that confers pathogen-inducible transcription to a reporter gene to which it is operably linked may be progressively deleted by 5', 3', and/or nested deletions until the effect of a pathogen on the reporter gene is diminished or eliminated. To confirm the identification of the pathogen-inducible element, point mutations may then be introduced into the element. An alternate approach to guage changes in transcription is to link the presumed regulatory element from the gene to the reporter gene. To test for complete promoters, the DNA fragment is placed directly in front of the reporter gene lacking endogenous promoter activity. Using such techniques, any fragment of an inducible plant disease resistance regulatory element may be identified.

By "tissue-specific" is meant capable of preferentially increasing expression of a gene product (e.g., an mRNA molecule or polypeptide) in one tissue (e.g., xylem tissue) as compared to another tissue (e.g., phloem).

By "cell-specific" is meant capable of preferentially increasing expression of a gene product (e.g., an mRNA molecule or polypeptide) in one cell (e.g., a parenchyma cell) as compared to another cell (e.g., an epidermal cell).

By "epi-5-aristocholene synthase" or "EAS" is meant an enzyme capable of catalyzing the cyclization of trans, trans-farnesyl diphosphate to the bicyclic intermediate epi-5-aristocholene.

By "pathogen" is meant an organism whose infection into the cells of viable plant tissue elicits a disease response in the plant tissue.

By "elicitor" is meant any molecule that is capable of initiating a plant defense response. Examples of elictors include, without limitation, one or more toxic ions, e.g., mercuric ions, other chemically defined compositions, metabolic inhibitors, cell wall glycans, certain glycoproteins, certain enzymes, fungal spores, chitosans, certain fatty acids, and certain oligosaccharides derived from plant cell walls, and elicitins (e.g., harpin, cryptogein, and pariscein).

By "elicitin" is meant a protein elicitor.

By "operably linked" is meant that a regulatory sequence (s) and a gene are connected in such a way as to permit gene expression when the appropriate molecules (e.g., transcriptional activator proteins) are bound to the regulatory sequence(s).

By "heterologous polypeptide" is meant any polypeptide that is expressed in a transformed plant cell from a gene that is partly or entirely foreign (i.e., does not naturally occur in) to the transformed plant cell.

By "polypeptide" is meant any chain of amino acids, regardless of length or post-translational modification (e.g., glycosylation or phosphorylation).

By "transformed plant cell" is meant a cell into which (or into an ancestor of which) a recombinant nucleotide sequence (e.g., the EAS4 promoter(−1147 to +67): GUS reporter gene or gEAS4$_{600}$(cyclase) promoter:parA1 mature elicitin gene) has been introduced by means of recombinant DNA techniques (e.g., those techniques described herein).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "transgenic" is meant any cell which includes a DNA sequence which is inserted by artifice into a cell and becomes part of the genome of the organism which develops from that cell. As used herein, the transgenic organisms are generally transgenic plants, and the DNA is inserted by artifice into the genome of the organism.

By "substantially pure DNA" is meant DNA that is free of the genes or ancillary nucleotides which, in the naturally-occurring genome of the organism from which the DNA of the invention is derived, flank the gene or regulatory element. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding an additional polypeptide sequence or a regulatory element.

Other features and advantages of the invention will be apparent from the following description of the preferred embodiments thereof, and from the claims.

BRIEF DESCRIPTION OF THE DRAWINGS

FIG. 2A presents a schematic of experiments carried out with the EAS4 promoter region controlling the expression of the GUS reporter gene in stably transformed transgenic plants. FIG. 2B presents the results of "gain of function" assays for the EAS4 promoter-associated sequences regulating expression of the GUS reporter gene via the CaMV 35S minimal promoter. In both FIGS. 2A and 2B, numbering for the EAS4 upstream region reflects numbering relative to the natural transcription start site of the EAS4 gene (see also SEQ ID NO:2 wherein the transcription start site corresponds to nucleotide 573). In both FIGS. 2A and 2B, the GUS expression is measured in fluorescence units per milligram of protein.

FIGS. 3A–3B are schematic illustrations showing the DNA sequence of the 5' upstream region of the EAS4 gene and the structure of the GUS reporter gene carrying the EAS4 promoter(−1148 to +67). FIG. 3A shows the nucleotide sequence of the 5' upstream region of the EAS4 promoter (−1148 to +67). The CAAT and TATA boxes are marked in bold face. The transcription initiation site is marked as +1. FIG. 3B is a schematic illustration showing the structure of the EAS4 promoter(−1148 to +67): GUS reporter gene. The 5' flanking sequence of the EAS4 promoter (−1148 to +67) was fused in correct reading frame with the GUS reporter gene in binary vector pBI101.1.

FIG. 4A is a graph illustrating elicitor-induced GUS activity in tobacco leaves over an 18 hour time course. 06i, 08r, and 09p each represent an independently transformed line of transgenic tobacco containing the EAS4 promoter(−1148 to +67): GUS reporter gene construct. Water (as control) and 25 nM of cryptogein were infiltrated symmetrically and simultaneously into the leaf (abaxially), and the infiltrated zones of leaf tissue were then collected for analysis of GUS activity over the 18 hour time course. The presented data are the averaged results of two separate experiments. FIG. 4B is a bar graph showing elicitor-induced GUS activity in the stems and roots of transgenic tobacco containing the EAS4 promoter(−1148 to +67): GUS reporter gene. 03f and 09p represent two independently transformed lines of transgenic tobacco. C-0 (open boxes) represents GUS activity present in segmented roots and stems without elicitor treatment. C-18 (shaded boxes) and E-18 (solid boxes) represent GUS activity in segmented roots and stems 18 hours after an incubation in water or 100 nM of elicitor cryptogein, respectively. Five independent plants were evaluated per transgenic line.

FIGS. 7A–7B show a Western blot analysis of induction of 5-epi-aristolochene synthase (EAS) in tobacco plant tissues. Proteins were extracted from control- and elicitor-treated tobacco leaves, stems, and roots. Equal guantities of proteins (25 µg per lane for leaf and stem, 15 µg per lane for root) were separated by SDS-PAGE and transferred to nitrocellulose membranes. The blots were then reacted with EAS antiserum and immunoreactive bands visualized using goat anti-mouse antibodies coupled to alkaline phosphatase. FIG. 7A shows the Western blot analysis of leaf and stem tissue samples. FIG. 7B shows the Western blot analysis of root tissue samples.

FIG. 8A is a color photograph showing elicitor-induced GUS activity in a transgenic tobacco leaf containing the EAS4 promoter(−1147 to +67): GUS reporter gene after treatment with two elicitor preparations: cryptogein and parasicein, both at concentrations of 25 nM and 50 nM (designated in FIG. 8A as $C_{25}$, $C_{50}$, $P_{25}$, and $P_{50}$, respectively). FIG. 8B is a color photograph of a leaf cross-section showing elicitor-induced GUS activity after treatment with cryptogein (magnification, 75×). FIG. 8C is a color photograph showing elicitor-induced GUS activity in a cross-section of a stem segment treated with cryptogein (magnification, 7.5×). FIGS. 8D–F are color photographs showing successively higher magnifications (15×, 60×, and 75×, respectively) of the GUS-stained stem cross-section shown in FIG. 8C. FIG. 8G is a color photograph showing a root tip treated with water and stained for GUS activity (magnification, 60×). FIG. 8H is a color photograph showing elicitor-induced GUS activity of a longitudinal section of a root tip treated with cryptogein (magnification, 60×). FIG. 8I is a color photograph of a longitudinal section of a root after treatment with water and staining for GUS activity (magnification, 75×). FIG. 8J is a color photograph showing GUS activity of a longitudinal section of a root treated with cryptogein (magnification, 75×). FIG. 8K is a color photograph of a root cross-section treated with water and staining for GUS activity (magnification, 95×). FIG. 8L is a color photograph showing GUS activity of a cross section of a root treated with cryptogein (magnification, 95×). C, denotes cryptogein; P, denotes parasicein; c, denotes cortex; ca, denotes cambium; e, denotes epidermis; p, denotes palisade parenchyma; pe, denotes periderm; ph, denotes phloem; pi, denotes pith parenchyma; s, denotes spongy parenchyma; t, denotes trichome; x, denotes xylem; vc, denotes vascular cylinder.

Figure 1:
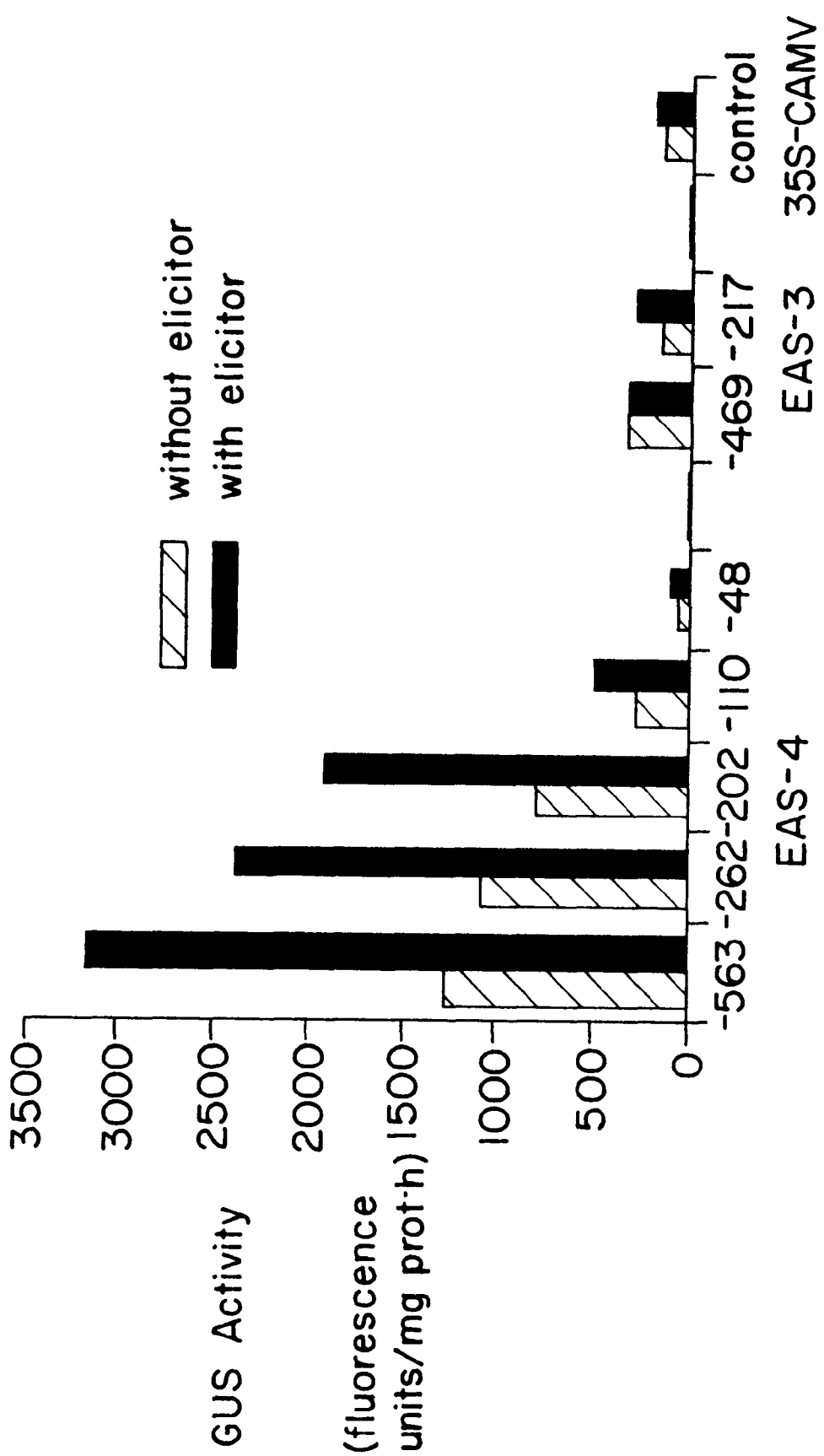
FIG. 1 presents data for transient expression experiments for GUS regulated by the EAS3 and EAS4 promoter region sequences in comparison to a CaMV 35S-GUS construct (Cauliflower Mosaic Virus 35S promoter—β-glucuronidase reporter gene). These experiments were carried out in tobacco protoplasts into which the DNA constructs had been electroporated. "Uninduced" levels of expression for the EAS-GUS constructs were relatively high because fungal enzymes which digest plant cell walls were used in the preparation of the protoplasts. The y-axis shows units of GUS activity and the 5' extents of the EAS upstream sequences are given below each bar on the graph. As above, the numbering is relative to the natural transcription start site of EAS4 (or the corresponding base of EAS3); in EAS4 (SEQ ID NO:2) a start site is at nucleotide 573; in EAS3 (SEQ ID NO:1) a potential transcription start site is at nucleotide 489.

Certain bacterial plant pathogens also express proteins with similar effects on the hypersensitivity response as those of the *P. parasitica* ParA1 elicitin. For the purposes of the present invention, these proteins fall within the scope of the term "elicitin." Multiple homologs of the avirulence gene avrBs3 of *Xanthomonas campestris* pv. *vesicatoria* have been detected in other *X. campestris* pathovars [Bonas et al. (1989) *Mol. Gen. Genet.* 218:127–136; Knoop et al. (1991) *J. Bacteriol.* 173:7142–7150] and in other species of Xanthomonas [De Feyter and Gabriel (1991) *Mol. Plant-Microbe Interact.* 4:423–432; Hopkins et al. (1992) *Mol. Plant-Microbe Interact.* 5:451–459]. The avrD gene of *Pseudomonas syringae* pv. tomato can confer avirulence; *P. syringae* pv. glycinea expresses an altered avrD gene product [Kobayashi et al. (1990) *Mol. Plant-Microbe Interact.* 3:103–111].

It is understood that to be useful in the present invention as it applies to creating transgenic plants with improved disease resistance traits using an elicitin coding sequence expressed under the regulatory control of a pathogen-response transcription regulatory element (and with a minimal promoter functional in those plants) that elicitin proteins must be capable of promoting expression of defense genes (including but not limited to those genes governing phytoalexin synthesis, the hypersensitive response and/or localized necrosis) in those plants. Many functional combinations of plant and phytopathogen are known to the art, and the skilled artisan knows how to test the functioning of a particular elicitin in a particular plant tissue (or cells) in the turning on of programmed cell death or phytoalexin synthesis or the like. It is also understood that treatment of plant cells or tissue with compositions such as certain fungal cellulases or certain plant polysaccharide fragments can also induce the host defensive (i.e., hypersensitive) response. Such treatments are used as models for actual plant pathogen attack or invasion.

A non-naturally occurring recombinant nucleic acid molecule, e.g., a recombinant DNA molecule, is one which does not occur in nature; i.e., it is produced either by natural processes using methods known to the art, but is directed by man to produce a desired result or it has been artificially produced from parts derived from heterologous sources, which parts may be naturally occurring or chemically synthesized molecules or portions thereof, and wherein those parts have been joined by ligation or other means known to the art.

A transgenic plant is one which has been genetically modified to contain and express heterologous DNA sequences, either as regulatory RNA molecules or as proteins. As specifically exemplified herein, a transgenic plant is genetically modified to contain and express a heterologous DNA sequence operably linked to and under the regulatory control of transcriptional control sequences by which it is not normally regulated, i.e., under the regulatory control of the inducible transcriptional control sequences of the EAS4 gene of *Nicotiana tabacum*. As used herein, a transgenic plant also refers to those progeny of the initial transgenic plant which carry and are capable of expressing the heterologous coding sequence under the regulatory control of the qualitative and/or quantitative transcription control sequences described herein. Seeds containing transgenic embryos are encompassed within this definition.

When production of a heterologous gene or coding sequence of interest is desired under conditions of potential pathogen invasion or inducer (e.g., elicitor) treatment, that coding sequence is operably linked in the sense orientation to a suitable promoter and under the regulatory control of the inducible regulatory sequences, in the same orientation as the promoter, so that a sense (i.e., functional for translational expression) mRNA is produced. A transcription termination signal functional in a plant cell can be placed downstream of the coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. Similarly, a heterologous coding sequence can be expressed under the regulatory control of the inducible transcription regulatory element or the transcription-enhancing element in transgenic plant cell suspension culture, with induction occurring in response to the addition of an elicitor to the cell culture medium.

Where inhibition of gene expression is desired in a plant being invaded by a microbial pathogen, such as a phytopathogenic fungus, then either a portion or all of that coding sequence or cDNA sequence can be operably linked to a promoter functional in plant cells, but with the orientation of the coding sequence opposite to that of the promoter (i.e., in the antisense orientation) so that the transcribed RNA is complementary in sequence to the mRNA, and so that the expression of the antisense molecule is induced in response to pathogen invasion. In addition, there may be a transcriptional termination signal downstream of the nucleotides directing synthesis of the antisense RNA.

The present inventors have isolated a DNA sequence which mediates the inducible expression of a downstream gene in plant cells in response to invasion by a potential plant pathogen and/or treatment with an elicitor or other chemical signals. For example, a combination of ethylene and methyl jasmonate may serve to induce downstream gene expression via the qualitative transcription regulatory sequence. It is understood that there may be a multiplicity of sequence motifs within that regulatory sequence, where individual motifs each respond to one or more distinct environmental signal. As specifically exemplified, this transcription-regulating sequence is derived from the EAS4 locus of *N. tabacum*, and it is given in SEQ ID NO:7. The deduced amino acid sequence for the EAS protein is given in SEQ ID NO:8. The open reading frame of the EAS4 gene, which is interrupted by six introns, is provided in SEQ ID NO:7.

A computer search of Genbank for nucleotide sequences homologous to the SEQ ID NO:2 sequence revealed no known nucleotide sequences with significant homology.

Organization of the EAS genes in the *N. tabacum* genome was described in Facchini and Chappell (1992) supra using an EAS probe and Southern hybridization experiments. Under conditions of high stringency, multiple fragments hybridized with analysis indicating that there is a gene family with some 12–16 members in the tobacco genome. In these experiments, however, the probe included the EAS coding sequence rather than the promoter and promoter-associated regulatory sequences.

EAS homologous genes can be identified and isolated from plant species other than *N. tabacum* based on significant degrees of nucleotide sequence homology; i.e., DNA:DNA hybridization under conditions of moderate to high stringency with a tobacco EAS coding sequence probe allows the identification of the corresponding gene from other plant species. A discussion of hybridization conditions can be found for example, in Hames and Higgins (1985) *Nucleic Acid Hybridization*, IRL Press, Oxford, U.K. Generally sequences which have at least about 70% nucleotide sequence homology can be identified by hybridization under conditions of moderate stringency. Under such conditions, it is generally preferred that a probe of at least 100 bases be used. Most preferably, in the present case, the probe will be derived from the coding portion of the EAS4 coding sequence. Labels for hybridization probes can include, but are not limited to, radioactive groups, fluorescent groups, and ligands such as biotin to which specific binding partners (which are in turn labeled) bind. It is the label which allows detection of the hybridization probe to the target nucleic acid molecule. Alternatively, well-known and widely accessible polymerase chain reaction (PCR) technology is advantageously used to amplify sequences with significant nucleotide sequence homology to a target sequence.

It is understood that nucleic acid sequences other than the EAS coding sequence disclosed in SEQ ID NO:7 will function as coding sequences synonymous with the exemplified EAS4 coding sequence. Nucleic acid sequences are synonymous if the amino acid sequences encoded by those nucleic acid sequences are the same. The degeneracy of the genetic code is well-known to the art; i.e., for many amino acids, there is more than one nucleotide triplet which serves as the codon for the amino acid. It is also well-known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Terpene cyclase genes can be found in solanaceous plants, including *N. tabacum* and *Hyoscyamus muticus*, as disclosed herein, and in members of the mint family (Labitaceae) and the Euphorbiaceae, including but not limited to those which have been demonstrated to contain sequences of significant homology, and in substantially all plants. Preferably, EAS4 homologs will be selected from the Solanaceae. Such sequences can be identified by nucleic acid hybridization experiments or when cloned in expression vectors, by cross reaction to tobacco EAS-specific antibody, or any other means known to the art, including the use of PCR technology carried out using oligonucleotides corresponding to portions of SEQ ID NO:7, preferably in the region encoding EAS. Antibody can be prepared after immunizing an experimental animal with EAS purified as described in Vogeli et al. (1990) *Plant Physiology* 93:182–187 or using a peptide conjugate, where the amino acid sequence of the peptide is taken from a hydrophilic portion of the EAS amino acid sequence (SEQ ID NO:8). Monoclonal and polyclonal antibody production techniques are readily accessible to the art (See, e.g., Campbell (1994) *Monoclonal Antibody Technology*. Laboratory Techniques in Biochemistry and Molecular Biology, Vol. 13, Burdon and Knippenberg, eds, Elsevier, Amsterdam; Harlow and Lane (1988) Antibodies: *A Laboratory Manual*, Cold Spring Harbor Laboratory, Cold Spring Harbor, N.Y.).

Alternately, a cDNA library (in an expression vector) can be screened with EAS-specific antibody, or EAS peptide-specific antibody can be prepared using peptide sequence(s) from hydrophilic regions of the EAS protein (SEQ ID NO:8) and technology well-known in the art.

An inducible transcription regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, CaMV). Truncated versions of other constitutive promoters can also be used to provide CAAT and TATA-homologous regions; such promoter sequences can be derived from those of *A. tumefaciens* T-DNA genes such as nos, ocs, and mas and plant virus genes such as the CaMV 19S gene. It will be understood that the goals of a skilled artisan will determine the choice of particular promoters used with the inducible transcription regulatory sequences. It is further understood that when a protein capable of generating a cell death response is to be expressed, then there is preferably no basal transcriptional (and translational) expression in the absence of inducer. The minimization of basal expression is less critical in applications for inducible gene expression where the gene product has no significant toxicity to the plant cells producing it.

A minimal promoter contains the DNA sequence signals necessary for RNA polymerase binding and initiation of transcription. For RNA polymerase II promoters, the promoter is identified by a TATA-homologous sequence motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from −90 to +8 of the 35S gene.

The inducible transcription regulatory sequence (qualitative transcription regulatory sequence) is localized to the region between −167 and −100 relative to the EAS4 transcription initiation site (nucleotides 406 to 473, initiation at nucleotide 573 in SEQ ID NO:2). It is understood that there may be a plurality of sequence motifs which respond to particular stimuli. Operably linking this sequence directly upstream of a minimal promoter functional in a plant cell confers inducible expression of a coding sequence operably fused just downstream of the promoter, e.g., a heterologous coding sequence, and the skilled artisan understands spacing requirements and other requirements for translational expression of the coding sequence. The heterologous coding sequence is preferably for an elicitin-like protein of a plant pathogenic microorganism (e.g., a virus, bacterium or fungus), for example, the sequence encoding the parA1 gene product (elicitin) of *Phytophthora parasitica* where disease resistance via the hypersensitivity response to an invading potential plant pathogen is desirable. Harpin proteins of certain phytopathogenic bacteria also can serve as inducers of expression mediated by the EAS4-derived inducible transcriptional regulatory sequences. Inclusion of additional 5' flanking sequence from the EAS4 gene allows for increased levels of downstream gene expression. Preferred is the use of a sequence including the −266 to +1 region of EAS4 (nucleotides 307 to 573 of SEQ ID NO:2), and more preferred is the sequence including −567 to +1 (nucleotides 1 to 573 of SEQ ID NO:2).

An alternative to the use of the fusion of the EAS4 transcription regulatory sequence fused to a heterologous minimal promoter is the use of the promoter region of EAS4 in conjunction with the upstream promoter-associated regulatory elements. In such an application the use of nucleotides 307 to 463, or more preferably for greater levels of downstream expression, nucleotides 371 to 463, 311 to 462, and 10 to 573 of SEQ ID NO:2.

In a plant such as *N. tabacum*, the instant inducible transcription regulatory element directs the induction of downstream gene expression in response to invading plant pathogens and certain compositions such as some fungal cellulases and certain plant and fungal cell wall fragments. Plant pathogens which can trigger this expression include, but are not limited to, Xanthominas, *Pseudomonas syringae*, Phytophthora species including *parasitica*, and Peronospora species (e.g., *tabaci*).

Coding sequences suitable for expression in a plant are operably linked downstream of the regulated promoter construct. Transgenic plants can be constructed using the chimeric gene consisting essentially of the regulated promoter, any additional transcription-enhancing sequences, and the desired coding sequence including the necessary sequence signals for its translation. Where disease resistance is to be advantageously induced in response to invasion of a transgenic plant tissue by a potential plant pathogen or in response to treatment with an elicitor or other chemical signal which induces EAS4 gene expression, the coding sequence is preferably for an elicitin of a plant pathogenic microorganism, e.g., the parA1 gene product of *Phytophthora parasitica* (as described in Kamoun et al. (1993) supra). Other elicitin-like proteins have been described in the readily available scientific literature, and include those from Phytophthora species, Peronospora species, and Xanthomonas species, among others.

Alternative coding sequences which can be expressed under the regulatory control of the present inducible transcription regulatory element for improvement of the resistance of a (transgenic) plant or plant tissue exposed to a viral, bacterial or fungal plant pathogen include, but are not limited to, chitinase, TMV coat protein or other plant virus coat protein, NIa virus gene and others.

Additionally, or alternatively, induction of the regulated construct can be induced, for example, by treating the transgenic plant or tissue with an elicitor or with a bacterium, virus or fungus (preferably not pathogenic for the host plant) capable of inducing expression via the inducible transcription regulatory element of a coding sequence not capable of turning on the HR, or disease resistance directly could be achieved. Coding sequences which may be advantageously expressed include an insecticidal protein, such as one of the *Bacillus thuringiensis* crystal proteins, which when expressed would protect the plant from insect pests.

Phytoalexin synthesis from the native EAS4 gene, or induction of gene expression mediated by the present regulated EAS4 promoter or the inducible transcription regulatory element in combination with at least a heterologous minimal promoter, can be induced by treating the plant tissue or cells with a wide variety of defined chemicals, crude fungal culture filtrates, fungal cell wall extracts, and oligosaccharides from plant or fungal cell walls [Albersheim and Valent (1978) *J. Cell. Biol.* 78:627–643]. Other compounds capable of inducing the HR include certain cellulases, for example, *Trichoderma viride* cellulases, and certain plant or fungal cell wall fragments, among others.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:273; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Sci.* 244:1293; Leemans (1993) *BiolTechnology.* 11:522; Beck et al. (1993) *Bio/Technology.* 11:1524; Koziel et al. (1993) *Bio/Technology.* 11:194; and Vasil et al. (1993) *BiolTechnology.* 11:1533.). Techniques are well-known to the art for the introduction of DNA into monocots as well as dicots, as are the techniques for culturing such plant tissues and regenerating those tissues. Monocots which have been successfully transformed and regenerated include wheat, corn, rye, rice and asparagus. For example, U.S. Pat. No. 5,350,689 (1994, Shillito et al.) describes transgenic *Zea mays* plants regenerated from protoplasts and protoplast-derived cells. For efficient production of transgenic plants, it is desired that the plant tissue used for transformation possess a high capacity for regeneration. Transgenic aspen tissue has been prepared and transgenic plants have been regenerated [Devellard et al. (1992) *C.R. Acad. Sci. Ser.* VIE 314:291–298K; Nilsson et al. (1992) *Transgenic Res.* 1:209–220; Tsai et al. (1994) *Plant Cell Rep.* 14:94–97]. Poplars have also been transformed [Wilde et al. (1992) *Plant Physiol.* 98:114–120]. Technology is also available for the manipulation, transformation and regeneration of Gymnosperm plants in the laboratory. For example, U.S. Pat. No. 5,122,466 (1992, Stomp et al.) describes the bio-ballistic transformation of conifers, with preferred target tissue being meristematic and cotyledon and hypocotyl tissues. U.S. Pat. No. 5,041,382 (1991, Gupta et al.) describes enrichment of conifer embryonal cells.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene.

Other techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment, or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

The transcription regulatory sequences, particularly the inducible transcription regulatory element (or the EAS4 promoter with the inducible and preferably the transcription-enhancing element) is useful in controlling gene expression in transgenic plant cells in suspension cell culture as an alternative to expression in transgenic plants. For example, the EAS4 promoter including the transcription initiation signals, the inducible transcription regulatory element and the transcription-enhancing element, can be used to mediate the inducible expression of one or more heterologous coding sequence(s) in transgenic plant cells in suspension cell culture. When desired, expression of the coding sequence of interest is induced by the addition of an elicitor or other inducing chemical signal to the culture. Suspension culture cells respond to elicitors readily in comparison to intact plants. The heterologous coding sequence(s) can encode proteins which mediate synthesis of pharmaceutical compounds, poly-β-hydroxybutyrate synthesis or other secondary metabolites, cellulose, starch, sugars, oils, or the heterologous sequences can encode pharmaceutical proteins, insecticidal toxin proteins, antifungal proteins, antiviral proteins (such as coat proteins to mediate resistance to virus infection), the N1a protein, chitinases, glucanases, male sterility proteins or sequences, proteins to improve nutritional quality or content, or developmental and/or tissue-specific programs or patterns. It is understood that transgenic plants can be similarly used to express heterologous coding sequences as can transgenic plant cells.

Where transgenic plants are to be induced for phytoalexin synthesis or for the expression of a heterologous coding sequence under the regulatory control of the EAS4 promoter or the inducible transcription regulatory element derived therefrom and/or the transcription-enhancing sequence derived from the EAS4 promoter as well, the elicitor must penetrate the cuticle of the plant to have an inductive effect. Alternatively, the plant tissue can be wounded to facilitate or allow the uptake of the elicitor into the plant tissue. A wide variety of inducing compositions, including elicitors and other chemical signals, such as the combination of ethylene and methyl jasmonate, can be effectively introduced into the transgenic plant suspension cell cultures, where there is significantly less of a barrier to the uptake and/or sensing of the elicitors. Where ethylene and methyl jasmonate serve to induce gene expression, the ethylene is used at a concentration between about 1 and about 50 ppm and the methyl jasmonate is used at a concentration between about 0.1 mM and about 1 mM.

The following examples use many techniques well-known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview; N.Y.; R. Wu (ed.) (1993) *Methods in Enzymology* 218; Wu et al. (eds.) *Methods in Enzymology* 100 and 101; Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) *Methods for Plant Molecular Biology*, Academic Press, San Diego, Calif; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 10:12; Davey et al. (1989) *Plant Mol. Biol.* 13:273; Walden and Schell (1990) *Eur. J. Biochem.* 192:563; Joersbo and Brunstedt (1991) *Physiol. Plant.* 81:256 and other work cited in the foregoing references. Abbreviations and nomenclature, where employed, are deemed standard in the field and are commonly used in professional journals such as those cited herein.

All references cited in the present application are expressly incorporated by reference herein.

The following examples are provided for illustrative purposes and are not intended to limit the scope of the invention as claimed herein. Any variations in the exemplified compositions and methods which occur to the skilled artisan are intended to fall within the scope of the present invention.

EXAMPLES

Example 1

EAS-specific Antibodies

Monoclonal and polyclonal antibodies specific for tobacco EAS were prepared as described by Vogeli et al. (1990) *Plant Physiology* 93:182–187. Additional antibody preparations could be made as polyclonal antibodies using purified EAS as antigen or using a peptide sequence conjugated to a carrier protein using well-known techniques. The amino acid sequence of a peptide for antibody production is selected from a particularly hydrophilic region of the protein (For antibody production techniques, see, for example, Campbell (1994) *Monoclonal Antibody Technology. Laboratory Techniques in Biochemistry and Molecular Biology*, Vol. 13, Burdon and Rnippenberg, eds, Elsevier, Amsterdam; Harlow and Lane (1988) *Antibodies: A Laboratory Manual*, Cold Spring Harbor Laboratory, Cold Spring Harbor, N.Y.).

Example 2

DNA and Protein Sequence Determination

Sequence determinations of single-stranded and double stranded DNAs were carried out by the dideoxynucleotide chain termination procedure [Sanger et al. (1977) *Proc. Natl. Acad. Sci. USA* 74:8073–8077], with a Sequenase kit from United States Biochemical Corp., Cleveland, Ohio) or an automated fluorescence based system (Applied Biosystems, Foster City, Calif.).

Example 3

Construction of a Full-Length EAS Clone

*Nicotiana tabacum* L. cv. KY14 cell suspension cultures were treated with *Trichoderma viride* cellulase (Type RS, Onozuka) at a final concentration 0.5 μg/ml during rapid growth phase to induce the expression of EAS. Parallel suspension cell cultures which did not receive cellulase served as controls. Cells were collected by gentle vacuum filtration 4 hours after the addition of the cellulase elicitor to the induced culture.

A cDNA library was prepared in pcDNAII (Invitrogen, San Diego, Calif.) from polyA$^+$ RNA extracted from the *N.*

*tabacum* cells treated for 4 hours with elicitor. The library was screened by differential hybridization using polyA+ RNA prepared from the induced and control cultures. Clones appearing to be positive were further screened by hybrid selection-in vitro translation-immunoprecipitation analysis as described by Alwine et al. (1979) *Methods Enzymol.* 68:220–242.

A putative positive EAS cDNA clone was used as a hybridization probe for the isolation of additional cDNA and genomic clones. The genomic library thus screened was one constructed in λEMBL3 using MboI partially digested DNA prepared from *N. tabacum* L. cv. NK326 hypocotyl DNA (Clontech, Palo Alto, Calif.). This screening yielded 8 independent clones, each of which appeared to represent a different chromosomal locus. EAS4 and EAS3 genomic clones were described in Facchini and Chappell (1992) supra, but are now known to have been incomplete.

Facchini and Chappell (1992) supra had misidentified the translation start sites of the EAS3 and EAS4 coding sequences in the genomic clone described therein. The correct translation start site for the EAS3 and EAS4 coding sequences have been determined to be methionine codons 165 bp upstream of the ATG codons previously identified as start sites. The corrected start site for EAS4 was mapped using a combination of primer extension assays to identify the transcription start site and additional N-terminal amino acid sequencing data of purified enzyme as noted hereinabove.

An amplimer of 110 bp was prepared by a polymerase chain reaction to provide a DNA sequence corresponding to amino acids 56–92 of the EAS4 protein (see SEQ ID NO:12) and Facchini and Chappell (1992) supra. This amplimer was used as a hybridization probe to screen a cDNA library in pcdNAII (Invitrogen, San Diego, Calif.) prepared from polyA+ RNA from tobacco cell culture cells 4 hours after elicitor treatment (*Trichoderma viride* cellulase). This amplimer was made using a sense primer (ATGCTGTTAGCAACCGGAAGG; SEQ ID NO:3) and a reverse primer (ATCCAAAATCTCATCAATTTC; SEQ ID NO:4), and the genomic EAS4 template in a standard PCR reaction [Saiki et al. (1988) *Science* 239:487–491]. The 110 bp amplimer was isolated after polyacrylamide gel electrophoresis using DE-81 paper (Whatman International, Inc., Clifton, N.J.). The isolated fragment was then radiolabeled with [α-$^{32}$P]-dCTP using a random priming kit from Stratagene (La Jolla, Calif.) for use as a hybridization probe in colony lifts of the cDNA library as previously described [Hanahan and Meselson (1980) *Gene* 10:63–67]. The longest clone obtained in these experiments appeared to lack 80 bp of 5' coding sequence.

To obtain a full-length clone, a RT/PCR approach was used. First strand cDNA was prepared from polyA+ RNA prepared from tobacco cells after induction with elicitor as described [Facchini and Chappell (1992) supra] using reverse primer having the sequence ATGAGTCCTTACAT-GTGA (SEQ ID NO:5). This sequence corresponds to nucleotides 459–477 downstream of the translation start site. The reverse transcriptase reaction was carried out in a 10 μl reaction (1 μg polyA+ RNA, 25 pmol reverse primer, 10 mM DTT, 2.5 mM each dATP, dGTP, dCTP, dTTP, 8 units RNase Block I (Stratagene, La Jolla, Calif.), first strand synthesis buffer used according to the manufacturer's instructions (Stratagene) for 1 hr at 37° C. This reaction was terminated by treating at 99° C. for 5 min. Then 40 μl of master PCR mix was added to the first strand reaction; PCR master mix contains 10 mM Tris-HCl pH 8.3, 50 mM KCl, 1.5 mM MgCl$_2$, 0.01% Tween-20, 0.01% (w/v) gelatin, 0.01% NP-40, 2.5 mM each deoxynucleotide triphosphate, 1 unit of TaqI polymerase, and 25 pmol forward primer (GGGAGCTCGAATTCCATGGCCTCAGCAGCAGCAG TTGCAAACTAT, SEQ ID NO:6, EcoRI and NcoI recognition sites underlined and ATG translation start site in bold). PCR was carried out under standard conditions [Back et al. (1994) *Arch. Biochem. Biophys.* 315:523–532]

The 492 bp reaction product was digested with EcoRI and HindIII and subcloned into similarly cut pBluescript SK (Stratagene). A HindIII/XhoI fragment from another partial cDNA clone was subsequently cloned into the corresponding sites of the 5'-terminal sequence clone to generate a full-length cDNA clone named PBSK-TEAS. pBSK-TEAS DNA was transformed into *Escherichia coli* TB1 using a CaCl$_2$ protocol [Sambrook et al. (1989) supra]. Determination of the DNA sequence of the insert confirmed that this plasmid had the expected and desired structure (dideoxynucleotide chain termination procedure, United States Biochemical Corp., Cleveland, Ohio).

Example 4

Identification of EAS Homologous Sequences

Tobacco leaf genomic DNA was isolated as described in Murray and Thompson (1980) *Nucleic Acids Research* 8:4321–4325. After digestion of aliquots with desired restriction enzymes, the digested DNA samples were electrophoresed on 0.8% agarose gels and the size-separated DNAs were transferred to nylon membranes. DNA blots were hybridized with random primer radiolabeled cEAS1, which is truncated at the 5' end of the coding region, (prepared as in Sambrook et al. (1989) supra) at 60° C. in 0.25 M sodium phosphate buffer, pH 8.0, 0.7% SDS, 1% bovine serum albumin, 1 mM EDTA. The blot was then washed twice at 45° C. with 2x SSC, 0.1% SDS and twice with 0.2x SSC, 0.1% SDS (1x SSC is 0.15 M NaCl, 0.015 M sodium citrate, pH 7.0). Relative hybridization levels were estimated from autoradiograms using a video densitometer (MilliGen/Biosearch, Ann Arbor, Mich.).

Facchini and Chappell (1992) supra reported that Southern hybridization results indicated that there were 12–16 copies of EAS-homologs in the *N. tabacum* genome. To address the presence of significantly homologous sequences to tobacco EAS and apparent number of copies per genome of those sequences, Southern hybridization experiments were carried out using DNA isolated from other plant species.

Restriction endonuclease-digested genomic DNAs are separated by agarose gel electrophoresis (0.8% agarose), and then transferred to a Hybond-N$^+$ membrane (Amersham Corp., Arlington Heights, Ill.). Radiolabeled probe comprising coding sequences of EAS, and hybridizations are carried out essentially as described in Sambrook et al. (1989) supra. Moderate stringency conditions are used (hybridization in 4x SSC, at 65° C.) last wash in 1x SSC, at 65° C.).

Alternatively, PCR can be carried out using target DNA as template and primers derived from the EAS4 coding sequence in highly conserved regions (see SEQ ID NO:7) using well-known techniques.

Example 5

Detection of EAS Protein

The enzymatic activity of an expression product can be confirmed using the techniques described in Facchini and Chappell (1992) supra and in Back et al. (1994) *Arch. Biochem. Biophys.* 315:527–532.

For detecting the presence of EAS cross-reacting protein material, total protein fractions are prepared from 100 µl aliquots of bacterial culture harvested and concentrated by centrifugation for 2 minutes in a microfuge. After discarding the culture supernatant, cell pellets are resuspended in 100 µl 50 mM Tris-HCl, pH 6.8, 10 mM dithiothreitol, 2% sodium dodecyl sulfate, 0.01% bromophenol blue, 10% glycerol. For immunological detection 15 µl aliquots are electrophoresed over 11.5% SDS-polyacrylamide gels; for Coomassie blue-staining of the proteins, 35 µl aliquots are similarly electrophoresed. For soluble protein samples, the cells are processed as in the procedure for determination of enzymatic activity (see Back et al. (1995) supra or Facchini and Chappell (1992) supra). For immunological detection 10 µl aliquots are electrophoresed as above; for Coomassie blue-staining, 10–50 µl aliquots were electrophoresed.

After electrophoresis the proteins are stained with Coomassie blue, or the proteins are transferred to nitrocellulose membranes as described [Towbin and Gordon (1984) *Journal of Immunological Methods* 72:313–340] for immunodetection. After incubating for 30 minutes in 5% low-fat milk in 1× TBS (20 mM Tris-HCl, pH 7.5, 500 mM NaCl), the nitrocellulose blots were incubated overnight in the same solution containing monoclonal antibody specific for tobacco EAS (1:1000 dilution; Vogeli et al. (1990) *Plant Physiology* 93:182–187). Goat anti-mouse antibodies linked to alkaline phosphatase and the specific chromogenic dye were then incubated to visualize the binding of the EAS-specific antibody to the proteins immobilized on the nitrocellulose membranes [Leary et al. (1983) *Proc. Natl Acad. Sci. USA* 80:4045–4049].

Example 6

Genomic EAS4 Clone

The 5'-truncated cDNA clone cEAS1 described in Facchini and Chappell (1992) supra was used as a hybridization probe for screening a *N. tabacum* cv. NK326 genomic library in the λEMBL3 vector (Clontech, Palo Alto, Calif.). DNA sequences were determined using routine subcloning and DNA sequencing protocols.

The DNA and deduced amino acid sequences of the EAS4 genomic clone are presented in SEQ ID NO: 7–8.

Example 7

Generation of Transgenic Plants

For studies of the function of portions of the upstream untranslated region of the EAS4 gene, HindIII/BamHI-ended fragments of this upstream DNA were cloned into pBI101 (Clontech, Palo Alto, Calif.) so that expression of the β-glucuronidase (GUS) reporter gene could be monitored in transformed plant cells. The 5'-flanking sequence of the EAS3 gene is given in SEQ ID NO:1 and the 5'-flanking sequence of the EAS4 gene is given in SEQ ID NO:2. In each of these sequences, the translation start site (ATG) is the last three nucleotides. By primer extension techniques, the EAS4 transcription start site was estimated at nucleotide 573 in SEQ ID NO:2. CAAT and TATA box motifs are identified at nucleotides 429 to 432 and at nucleotides 456 to 459 in SEQ ID NO:1 (EAS3) and at nucleotides 513 to 516 and at nucleotides 540 to 543 in SEQ ID NO:2 (EAS4).

The transformed plant cell lines were produced using a modified *Agrobacterium tumefaciens* transformation protocol. The recombinant plasmids containing the sequences to be introduced into plant tissue were transferred into *A. tumefaciens* strain GV3850, by triparental mating with *E. coli* TB1 (pRK2013). *N. tabacum* leaves at a variety of stages of growth were cut into 1 $cm^2$ pieces, and dipped in a suspension of agrobacterial cells (about $10^4$ to $10^5$ cells/ml). After 3 to 10 minutes, the leaf segments were then washed in sterile water to remove excess bacterial cells and to reduce problems with excess bacterial growth on the treated leaf segments. After a short drying time (30 to 60 seconds), the treated leaf segments are placed on the surface of Plant Tissue Culture Medium without antibiotics to promote tissue infection and DNA transfer from the bacteria to the plant tissue. Plant Tissue Culture Medium contains per liter: 4.31 g of Murashige and Skoog Basal Salts Mixture (Sigma Chemical Company, St. Louis, Mo.), 2.5 mg of benzylaminopurine (dissolved in 1 N NaOH), 10 ml of 0.1 mg/ml indoleacetic acid solution, 30 g sucrose, 2 ml of Gamborg's Vitamin Solution (Sigma Chemical Co., St. Louis, Mo.) and 8 g of agar. The pH is adjusted between pH 5.5 and 5.9 with NaOH. After 2 days, the leaf segments were transferred to Plant Tissue Culture Medium containing 300 µg/ml of kanamycin, 500 µg/ml of mefoxin (Merck, Rahway, N.J.). The kanamycin selects for transformed plant tissue, and the mefoxin selects against the agrobacterial cells.

It is necessary to minimize the exposure of the explant tissue to agrobacterial cells during the transformation procedure in order to limit the possible induction of the regulated parA1 coding sequence during the production of the transgenic plant cells, which would cause a cell death response. Accordingly, the bio-ballistic technique for the introduction of heterologous DNA containing cell suicide genes under the regulatory control of the inducible transcriptional regulatory element is a useful alternative transformation technique because it does not entail the use of agrobacterial cells or fungal cell wall digestive enzymes (as necessary for the generation of protoplasts for electroporation), both of which lead to induction of the coding sequences under the control of that regulatory element.

Transgenic plants were regenerated essentially as described by Horsch et al. (1985) *Science* 227:1229–1231.

The resulting transgenic plants were tested for the expression of the β-glucuronidase (GUS) reporter gene using 5-bromo-4-chloro-3-indolyl-β-D-glucuronic acid as described by Jefferson et al. (1987) *EMBO Journal* 6:3901–3907, using untreated (control) conditions and inducing conditions. An inducing condition is the intercellular application of *T. viride* cellulase to tobacco tissue in the transgenic plants (using a mechanical pipetter to apply 50–100 µl or 10–100 nm protein (e.g., cryptogein) inducing composition to interstitial tissue); controls were mock-applied but not treated with cellulase elicitor. Tobacco tissue was wounded with a scalpel in some experiments to facilitate exposure to the inducing compounds.

Example 8

Deletion Analysis of Promoter and Promoter-Associated Region

In separate reactions, the EAS4-derived DNA sequence encompassed by −567 to +67 relative to the transcription start site (nucleotides 6 to 642, SEQ ID NO:2, EAS4) was substituted for the Cauliflower Mosaic Virus (CaMV) 35S promoter [Benfey et al. (1990) *EMBO Journal* 9:1677–1684] in the GUS-reporter vector pBI221 (Clontech, Palo Alto, Calif.). Deletion mutants in the EAS4 upstream regions were then isolated after restriction endonuclease. Analysis of the gEAS promoter-GUS constructs was carried out in electroporated tobacco cell protoplasts (FIG. 1) and in stably transformed tobacco lines (FIG. 2A, Table 1). Preliminary data for the transient expression demonstrated that SEQ ID NO:1 did not function for elicitor inducibility and SEQ ID NO:2 functioned in regulating gene expression.

Figure 2A:
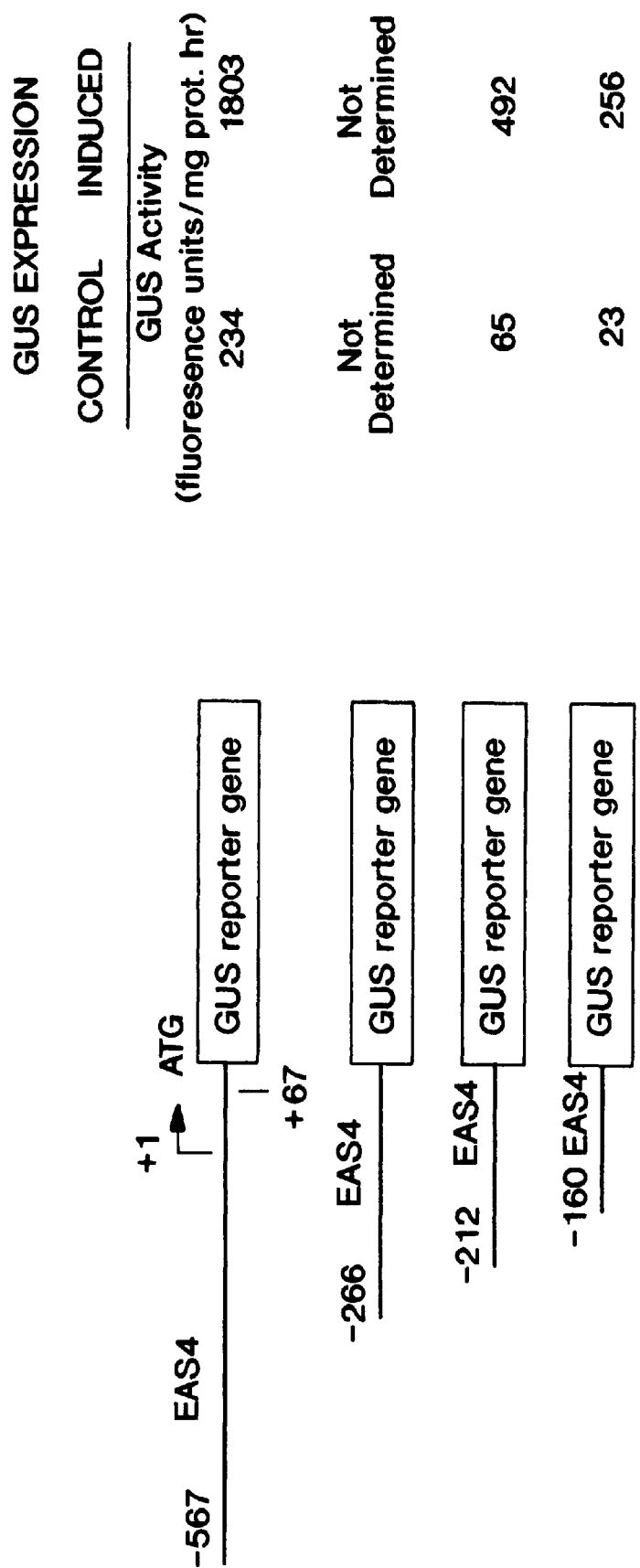
FIGS. 2A–2B present information concerning the reporter gene expression directed by the instant inducible transcription regulatory element of the invention.

The transient expression data obtained with the *N. tabacum* protoplasts into which various EAS3 and EAS4 promoter-GUS constructs were introduced are given in FIG. 1. Progressive deletions from the 5' end of the EAS4 promoter regions reduce the levels of expression, but inducibility is maintained for the −262, −202 and −110 constructs (relative to the transcription start site at nucleotide 573 of SEQ ID NO:2). These data indicated that only very low levels of GUS are expressed via either EAS3 promoter region construct. Similarly, the CaMV 35S promoter alone is not induced by the elicitor treatment.

Figure 2B:
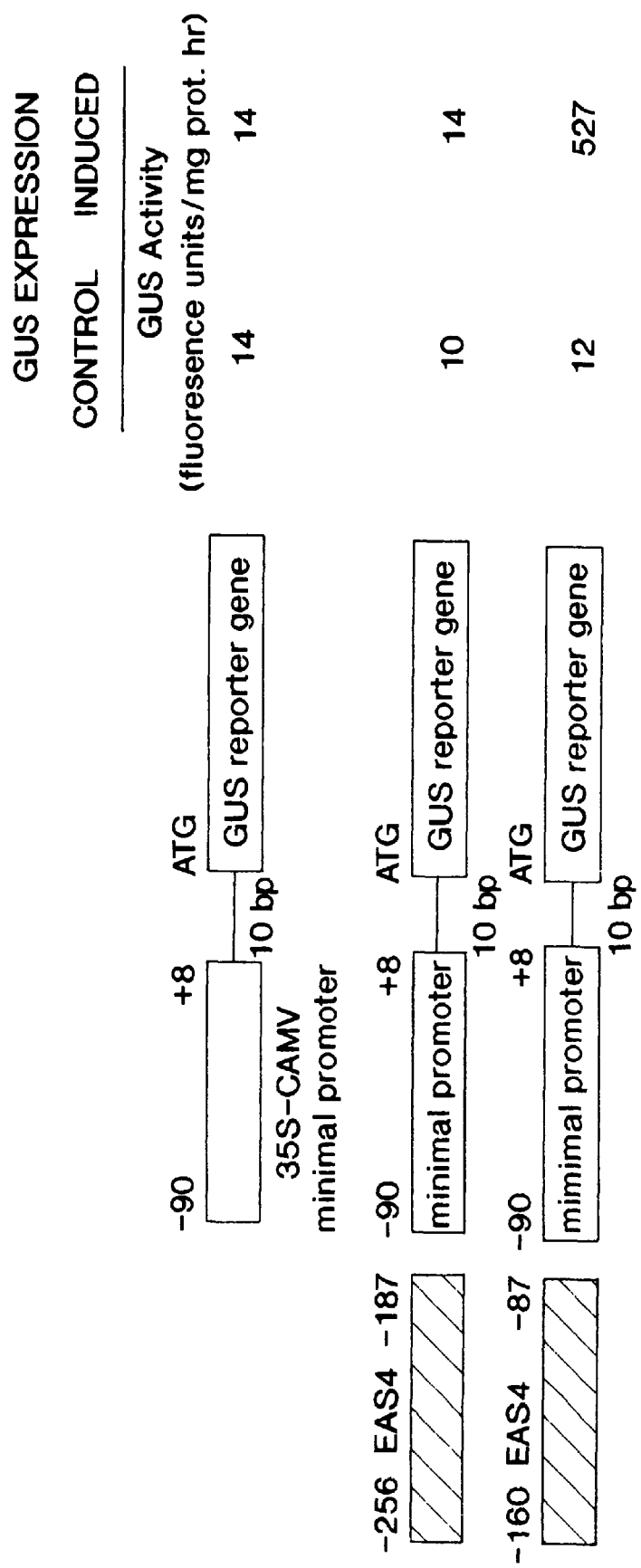

The data in FIGS. 2A–2B indicate that deletion of genetic material between −567 and −160 reduce the level of downstream gene expression but does not destroy the inducibility of expression. Therefore, the DNA sequences between −567 and −160 appear to contain transcription-enhancing activity. Most of the transcription-increasing activity appears to reside between −567 and −212, but additional enhancement appears to be mediated by sequence information between −212 and −160 relative to the transcription start site (transcription start site is nucleotide 573; −567 is nucleotide 1, −212 is nucleotide 361, and −160 is nucleotide 413, all in SEQ ID NO:2).

In the Gain of Function assay data in FIG. 2B, the DNA sequence information necessary to mediate induction in response to elicitor treatment is located between −160 and −87 relative to the EAS4 transcription start site (i.e., between nucleotides 413 and 486 of SEQ ID NO:2). In these experiments the EAS-derived sequences were placed in front of a truncated CaMV 35S promoter [Benfey et al. (1990) *EMBO J.* 9:1677–1684]. This figure also demonstrates that the EAS4-derived transcription regulatory region functions when fused to a heterologous minimal promoter.

In a more extensive analysis of independent transformants, either the entire −567 to +67 EAS4 upstream region or 5' deletions thereof were inserted upstream of the GUS (β-glucuronidase) reporter gene in vector pBI101 (Clontech, Palo Alto, Calif.), and expression levels of the GUS reporter were assayed under inducing and noninducing conditions. 160 bp upstream of the transcription start site of EAS4 were sufficient to direct the regulated expression of the GUS reporter gene, although the presence of additional upstream sequences mediated increased expression.

Constructs containing a minimum of 167 bp upstream of the EAS4 transcription start site gave transient gene expression in electroporated protoplasts and confer elicitor-inducibility of GUS reporter gene expression (minimum of 2.5-fold increase in gene expression). By contrast, the EAS3 upstream region (SEQ ID NO:1) does not appear to support high levels of reporter gene expression in the transient expression system, nor does it appear to confer elicitor-inducibility to the downstream reporter gene.

In part, the elicitor-inducible GUS reporter gene expression was expected in the protoplast system because those protoplasts were generated using fungal cell wall digestive enzymes, and those enzymes have been shown to elicit phytoalexin production and sesquiterpene cyclase gene expression in plants [Chappell et al. (1991) *Plant Physiology* 97:693–698]. A possible explanation as to why the protoplasts respond to a second elicitor treatment is that the cells are allowed to recover for 6–8 hours before the second treatment. This recovery phase allows the cells to return to an elicitor-responsive state.

pBI101 is commercially available from Clontech (Palo Alto, Calif.). It contains the CaMV 35S promoter upstream of the GUS reporter gene in a pUC19 vector; thus it serves as a vector for transient expression experiments where the recombinant vector is introduced into plant protoplasts. The presence of this plasmid and its derivatives is selected by growth on kanamycin. A "promoter-less" GUS cassette in the Agrobacterium binary plasmid vector pBIN19 (Bevan, M. (1984) *Nucl. Acids Res.* 12:8711) similarly carries a plant-expressible kanamycin resistance determinant.

Example 9

Identification of Inducible Transcription Regulatory Element

The 5' flanking domains of genomic EAS3 and EAS4 clones were mapped by S1 nuclease protection and primer extension experiments [Sambrook et al. (1989) supra]. Subclones comprising up to 1 kb 5' to the translation start site were sequenced and fused to the β-glucuronidase (GUS) reporter gene in pBI101 for studies in transgenic plant tissue. The resulting recombinant plasmids were then electroporated into tobacco protoplasts. GUS activity was measured in transient expression assays, and stable transformed tobacco cell lines were also isolated for studies of GUS induction and expression.

Constructs were prepared containing a minimum of about 200 bp of nucleotide sequence upstream of the EAS4 transcription start site in the modified pBI101 vector, and a β-glucuronidase (GUS) reporter gene were made and analyzed for ability to drive regulated GUS expression. 200 bp of flanking sequence appeared sufficient to drive transient gene expression in electroporated protoplasts and confers elicitor inducibility to GUS expression (minimum of 2.5 fold induction). Similar experiments with the EAS3 flanking sequence indicated that 200 bp from the EAS3 locus did not support either high levels of GUS expression or elicitor responsiveness in transformed plant cells. Cellulase and elicitins from *Phytophthora* [Ricci et al. (1989) *Eur. J. Biochem.* 183:555–563] serve to induce gene expression mediated by the EAS4-derived regulatory sequences.

Further studies related to the identification of sequences important in mediating induced gene expression in response to pathogen invasion, as modeled using cellulase or eliciting, were carried out after oligonucleotide site-directed mutagenesis [Kunkel (1985) *Proc. Natl. Acad. Sci. USA* 82:488–492] of the putative regulatory region of EAS4. Substitution of GT for the wild-type CA at −233 and −234 relative to the EAS4 transcription start site (nucleotides 334–335 of SEQ ID NO:2) did not appear to alter the expression of the GUS reporter gene as measured after incubation in the presence of elicitor (cellulase) for 20 hours.

Preliminary methylation interference and gel retardation studies carried out essentially as described [Sambrook et al. (1989) supra] indicated that an octameric sequence centered around −233 relative to the translation start site (centered around 334 of SEQ ID NO:2) binds proteins from plant cell nuclei. Methylation interference data suggested that the G at position −233 was preferentially protected against methylation by DMS (dimethyl sulfate) if first allowed to interact with nuclear extracts. The results of gel retardation studies were consistent with those obtained in the methylation protection experiments. When DNA fragments containing the −343 to −140 region (relative to the translation start site) (nucleotides 230 to 433 of SEQ ID NO:2) were examined after reaction to nuclear extracts, mobility in native acrylamide gel electrophoresis appeared retarded. Protein binding was abolished by the GT to CA substitution at positions −234 and −233. Similar results were observed in control and elicitor-induced cell extracts, and reporter gene expression was not changed by this 2 bp mutation. Thus, it is concluded that the region around −233 is not directly involved in the induction of gene expression in response to pathogen invasion or elicitor treatment.

Preliminary experiments indicate that EAS4 DNA sequences between −253 and −48 relative to the EAS4 transcription start site (between nucleotides 320 and 525 of SEQ ID NO:2) have qualitative and quantitative effects on downstream reporter gene expression. Sequences between −110 and −1 of EAS4 relative to the transcription start site of EAS4 (nucleotides 463 to 572 of SEQ ID NO:2) to mediate the inducible response, while sequences between −202 and −110 relative to the EAS4 transcription start site (nucleotides 371 to 463 of SEQ ID NO:2) enhance the levels of both induced and uninduced reporter gene expression.

Example 10

Construction of a Chimeric EAS4 Promoter(−1148 to +68): GUS Reporter Gene

In another series of experiments, we examined the activation of the EAS4 promoter (−1148 to +67) in transgenic tobacco plants. To obtain the 5' flanking sequence of the tobacco EAS4 gene promoter (−1148 to +67), an approximately 1.9 kb HindIII-HindIII fragment containing a portion of the EAS5' sequence was isolated from the gEAS4 genomic clone described above. The isolated fragment was then cloned into the polylinker of the pBluescript KS(+) plasmid vector (Stratagene). Using standard PCR methodology, the resulting pKS(+) plasmid containing the EAS4 HindIII-HindIII fragment was used as a DNA template to generate an approximately 1.2 kb EAS4 promoter subfragment (−1148 to +67) having sequences 1148 bp upstream and 67 bp downstream of the EAS4 transcription start site. The nucleotide sequence of this fragment is shown in FIG. 3A. The 1215 bp HindIII-BamHI fragment containing the EAS4 promoter (−1148 to +67) was then ligated in correct reading frame with the coding region of GUS in the binary vector pBI101.1. FIG. 3B shows a schematic illustration of the structure of the resulting EAS4 promoter(−1148 to +67): GUS reporter gene fusion.

Example 11

Elicitor- and Pathogen-inducible Expression of a Chimeric EAS4 Promoter(−1148 to +67): GUS Gene in Transgenic Tobacco To assess the function of the tobacco EAS4 promoter (−1148 to +67), gene expression of the GUS reporter construct shown in FIG. 3B in transgenic tobacco plants treated with either an elicitor or pathogen was monitored as follows.

The EAS4 promoter(−1148 to +67): GUS reporter gene shown in FIG. 3B was transferred to the disarmed *Agrobacterium tumefaciens* strain GV3850 using the triparental mating procedure described by Schardl et al. (Gene 61: 1–11, 1987). Tobacco plants (*Nicotiana tabacum* cv Xanthi) were then transformed with the disarmed Agrobacterium harboring the reporter construct using the leaf disc transformation method described by Horsch et al. (*Science* 227: 1229–1231, 1985). As control pkants, lines of transgenic tobacco expressing the GUS reporter gene under the control of the cauliflower mosaic virus (CaMV) 35S promoter were also regenerated. Seeds from regenerated transgenic tobacco plants were germinated on medium containing 100 mg/L kanamycin. The resulting kanamycin-resistant plants were subsequently transferred into soil and grown in a greenhouse. These plants were then tested for the expression of the GUS reporter gene using the assay described above, using untreated (water control) conditions and inducing (elicitor- and pathogen-treated) conditions.

To determine the elicitor inducibility of GUS gene expression driven by the EAS4 promoter(−1148 to +67), GUS activity was monitored in the leaves of transgenic tobacco plants treated with the fungal elicitor protein cryptogein or water as follows. Half of a fully expanded leaf (8th leaf from bottom of the plant) from a two-month old transgenic tobacco plant was infiltrated from the abaxial side using a pipette with approximately 50 μl of 25 nM cryptogein [prepared according to the method of Ricci et al., *Eur. J. Biochem.* 183: 555–563, 1989]; the other half of the leaf was infiltrated with approximately 50 μl of water in a similar fashion. At various times after infiltration, the cryptogein and water infiltrated zones of the leaf were collected from intact plants and analyzed for GUS activity.

Figure 4A:
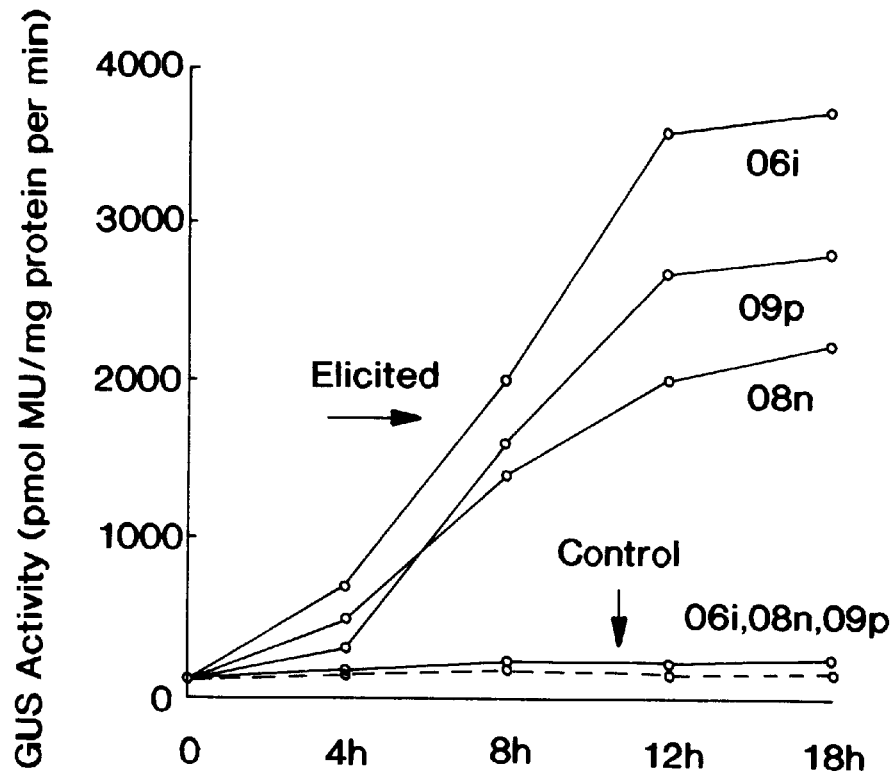
FIGS. 4A–4B present data concerning elicitor-induced GUS gene expression in leaves, stems, and roots of transgenic tobacco plants containing the EAS4(−1148 to +67): GUS reporter gene.
Figure 8A:
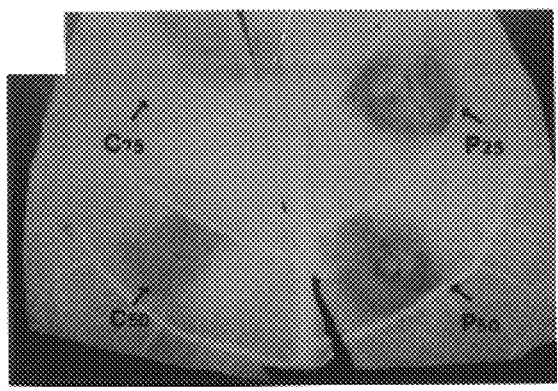
FIGS. 8A–8L are color photographs illustrating the histochemical localization of elicitor-induced GUS activity in transgenic tobacco containing the EAS4 promoter(−1147 to +67): GUS reporter gene. Leaf tissues from one representative line of transgenic tobacco were infiltrated with either 25 or 50 nM of the cryptogein elicitor. After an approximately 8 hour incubation, tissue sections were stained using 1 mM X-gluc(5-bromo-4-chloro-3-indoyl β-glucuronide) for analysis of GUS activity. Stem and root segments were incubated with water or 100 nM of the elicitor cryptogein for approximately 12 hours before staining.

As shown in FIG. 4A, leaves from three independent lines of transgenic tobacco which were infiltrated with 25 nM of cryptogein showed that GUS gene expression was induced ≈4 hours after elicitor treatment. In contrast, the 35S CaMV promoter: GUS reporter gene was not induced by elicitor treatment (data not shown). In addition, GUS activity was not induced in leaves of transgenic plants containing the EAS4 promoter(−1148 to +67): GUS reporter gene when treated with water (FIG. 4A). At the microscopic level, GUS activity was found to be restricted exclusively to areas of leaf tissue challenged with elicitor, indicating that the EAS4 promoter(−1148 to +67) was not induced by a secondary signal (FIG. 8A).

To characterize the organ-specificity of GUS gene expression driven by the EAS4 promoter (−1148 to +67), roots and stems of transgenic tobacco plants were treated with cryptogein elicitor and analyzed for GUS activity as follows. Roots were obtained from transgenic tobacco plants and maintained on sterile Murashige and Skoog medium until tested. Stems (removed from one to one and half inches under the apex) were obtained from two-month old greenhouse-grown transgenic tobacco plants. Prior to elicitor treatment, roots and stems were cut into ≈15–30 μM segments. Segmented roots and stems were then incubated on filter paper moistened with 100 nM of cryptogein or water for 18 hours at room temperature. GUS activity in root and stem segments was subsequently analyzed using the assay described above.

Figure 4B:
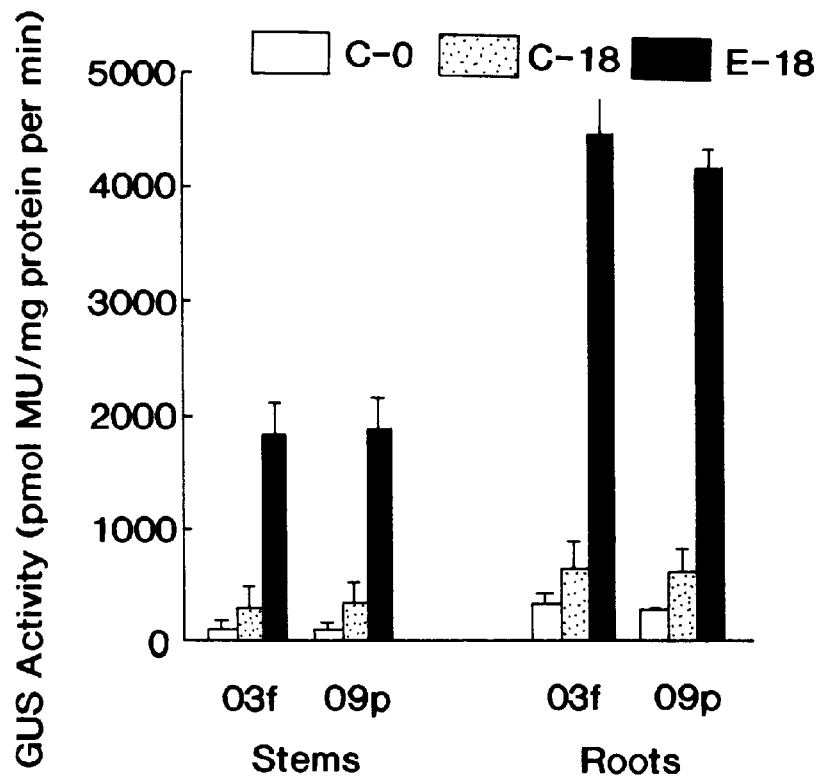

FIG. 4B shows that GUS activity was induced in both the roots and stems of two independent lines of transgenic tobacco after an 18 hour treatment with cryptogein. A 15-fold increase in GUS activity relative to samples treated with water (control) was observed in both stems and roots, respectively. Roots showed higher GUS activity than stems. These results show that the EAS4 promoter (−1148 to +67) is inducible in root and stem tissue in response to elicitor treatment.

To determine if the EAS4 promoter(−1148 to +67): GUS reporter gene was induced by fungal pathogens, GUS activity in the leaves of transgenic tobacco treated with two different races of *Phytophthora parasitica* var. Nicotianae was analyzed as follows. Young apical leaves were detached from about 45-day old transgenic tobacco plants and inoculated with a mycelial plug (≈1 cm in diameter) of 2-day-old race 0 or race 1 of *Phytophthora parasitica* var. Nicotianae cultures grown on oatmeal agar as described by Tedford et al. (*Plant Disease* 74: 313–316, 1990). Inoculated leaves were then incubated on filter paper moistened with distilled water in a growth chamber at 25° C. with constant fluorescent light for 24 hours. Control leaves were inoculated with blank oatmeal agar plugs. Inoculated tissues were subsequently collected and analyzed for GUS activity as described above.

Figure 5:
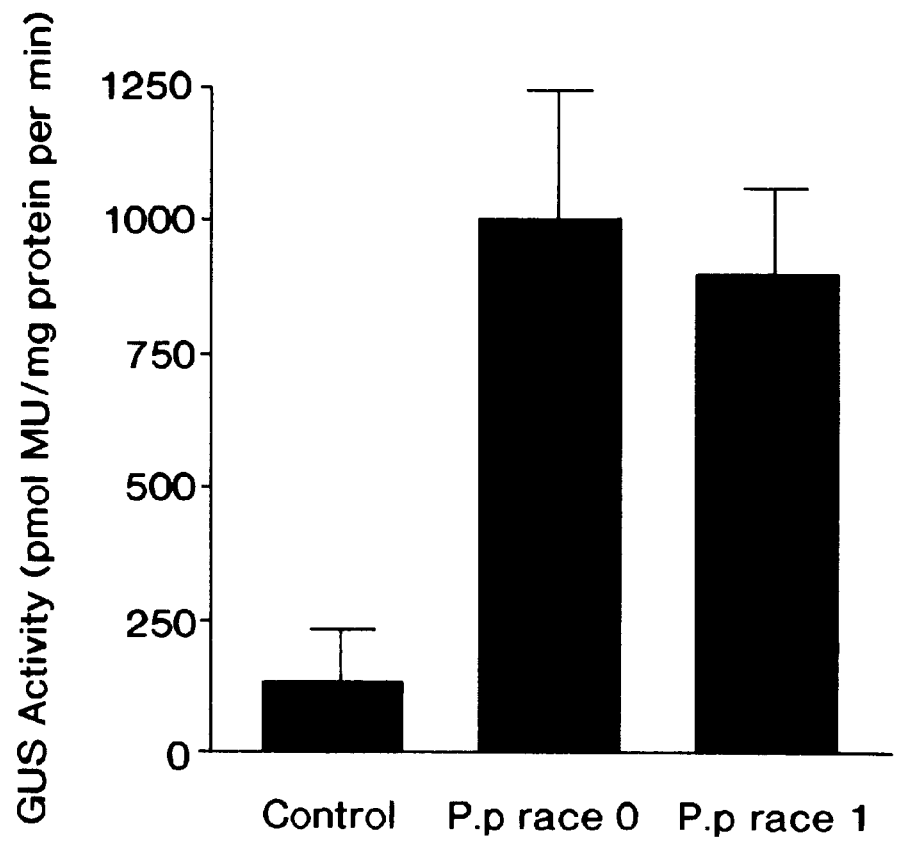
FIG. 5 is a bar graph illustrating pathogen-induced GUS activity by race 0 and race 1 of *Phytophthora parasitica* var. Nicotianae in transgenic tobacco. Detached leaves from one line of transgenic tobacco (09p) containing the EAS4 promoter(−1148 to +67): GUS reporter gene were inoculated with mycelial plugs of 2-day-old P. p. var. Nicotianae cultures and then incubated in a growth chamber at 27° C. with constant fluorescent light for 24 hours. Control leaves were inoculated with sterile oatmeal agar plugs. Infected zones of tissue were then examined for GUS activity. Values indicated by each bar are the means and standard errors for three separate experiments (n=5).

As shown in FIG. 5, GUS activity was induced in the leaves of transgenic tobacco when treated with either race 0 or race 1 of *Phytophthora parasitica* var. Nicotianae. Although race 0 and race 1 of P. p. var. Nicotianae typically induce different disease symptoms, no significant difference in disease symptoms caused by these two races was observed on the transgenic leaves of *N. tabacum* cv. *Xanthi*. Furthermore, we observed that both race 0 and race 1 of *P. parasitica* induced the expression of the GUS reporter gene equally well.

To determine if GUS gene expression was induced by bacterial pathogens or elicitors, GUS activity in the leaves of transgenic tobacco treated with *Pseudomonas syringae* pv. Syringae 61 and its hrpH mutant, and *Erwinia amylovora* harpin elicitor was analyzed as follows. Young apical leaves were detached from an approximately 45 day old transgenic tobacco plant and infiltrated with a cell suspension ($A_{600}$= 0.05) of *Pseudomonas syringae* pv. Syringae 61 or its hrpH mutant, or harpin elicitor (50 µg/ml) using a pipette according to the methods described above. Control leaves were infiltrated with water. After approximately 12 hours, tissue was collected and analyzed for GUS activity as described above.

Figure 6:
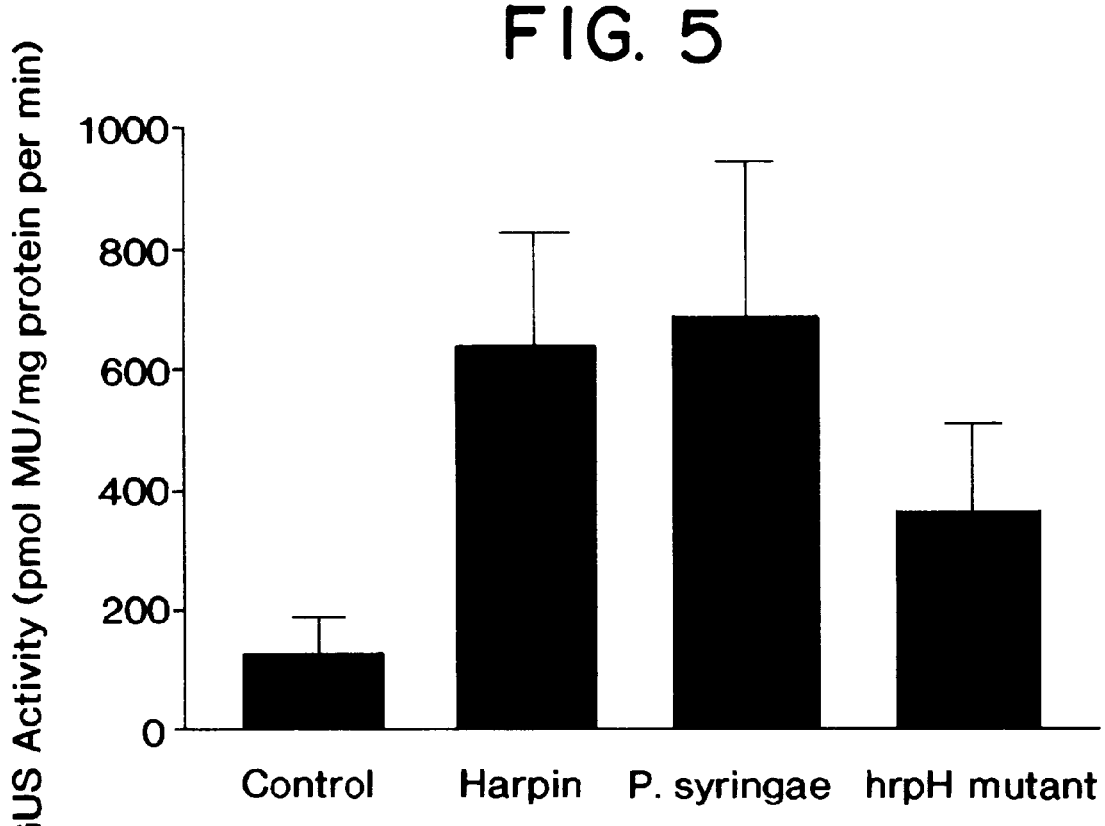
FIG. 6 is a bar graph illustrating the comparison of pathogen- and elicitor-induced GUS activity in transgenic plants treated with *Pseudomonas syringae* pv. Syringae 61 and its hrpH mutant, and the purified bacterial elicitor protein harpin. Leaves of one line of transgenic tobacco (09-P) containing the EAS4 promoter(−1148 to +67): GUS reporter gene were infiltrated with either 50 µg/mL of purified *Erwinia amylovora* harpin elicitor, cell suspensions of wild type *P. syringae* pv. Syringae 61 or its hrpH mutant ($A_{600}$=0.05). After a 12 hour incubation, infiltrated zones of tissue were subsequently analyzed for GUS activity. Control values represent GUS activity observed in leaf tissue samples which were infiltrated with water. Values indicated by each bar are the average of results obtained from five plants.

As shown in FIG. 6, GUS activity was induced in the leaves of transgenic tobacco after 12 hours when treated with either Pseudomonas, hrpH mutant, or harpin elicitor. In contrast, low GUS activity was detected in transgenic leaves treated with water. Furthermore, a hypersensitive response was observed to develop within the tissue zones infiltrated with either wild type *P. syringae* Pv. Syringae 61 or purified harpin protein about 12–15 hours after treatment. These results indicate that the EAS4 promoter (−1148 to 67) is activated in response to either bacterial pathogens or a bacterial-derived elicitor.

Example 12

Immunoblot Analysis

The expression of EAS in different tissues of transgenic plants in response to cryptogein treatment was analyzed by standard Western blotting methods as follows. Proteins were extracted from control and cryptogein elicitor-treated tobacco tissues by homogenization with 80 mM potassium phosphate buffer (pH 7.0) containing 20% (w/v) glycerol, 10 mM sodium metabisulfite, 10 mM sodium ascorbate, 15 mM $MgCl_2$, and 5 mM β-mercapthoethanol as described by Vogeli and Chappell, (supra). Protein concentrations were determined by the Bio-Rad assay. Equal quantities of protein were then separated by SDS-PAGE, transferred to nitrocellulose membranes, and immunodetected as described by Voegeli and Chappell (supra).

As shown in FIGS. 7A–B, EAS protein was not detected in the leaves of tobacco plants by Western blotting experiments. In contrast, EAS protein was induced in the leaves of transgenic plants after treatment with elicitor. In segmented stems and roots, EAS protein was detected in the absence of elicitor treatment, indicating that one or more members of the EAS multigene family, but not EAS4 as determined by histochemical localization data described above, are activated upon wounding.

Example 13

Cell-Specific Expression Pattern of the EAS4 Promoter(−1148 to +67): GU8 Reporter Gene in Transgenic Tobacco FIGS. 8A–K show the results obtained when tissues from different transgenic lines of tobacco were stained for GUS activity after treatment with elicitins. The data presented in FIGS. 8A–K are representative of a series of observations made at different times with several independent lines of transgenic tobacco expressing the EAS4 promoter(−1148 to +67): GUS reporter gene shown in FIG. 3B. GUS activity was localized in transgenic tissues by staining sections with 1 mM X-gluc (5-bromo-4-chloro-3-indolyl β-glucuronide) staining solution containing 50 mM $NaPO_4$, pH 7, 0.05% Triton X-100, and 0.1% β-mercaptoethanol for 12–16 hours at 37° C., and then fixed in 50% ethanol, 5% glacial acetic acid, and 10% formaldehyde for 2 hours. Chlorophyll was removed from appropriate tissues by incubating the sections in 70% ethanol. Sections of stained plant tissue were observed using a Zeiss IIIRS microscope and photographed using an MC63 photomicrographic camera.

Figure 8B:
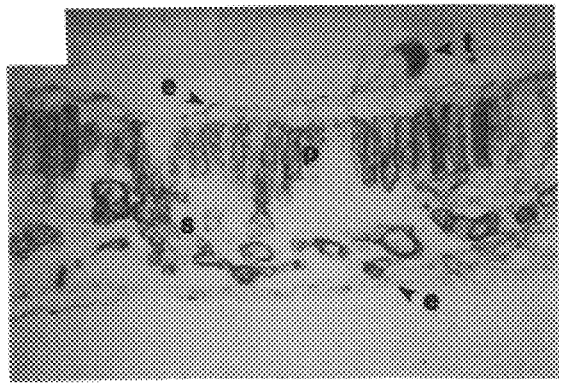
Figure 8C:
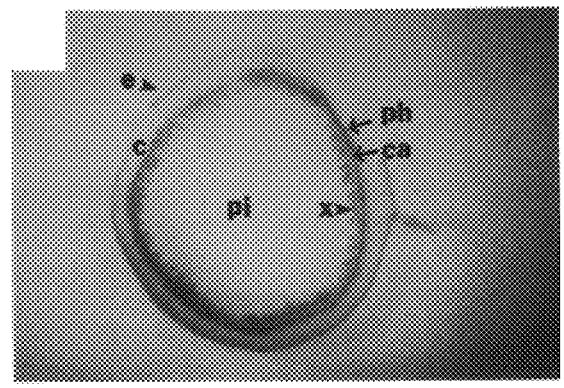
Figure 8D:
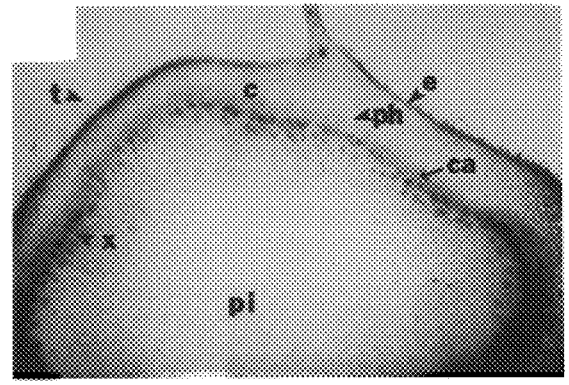
Figure 8E:
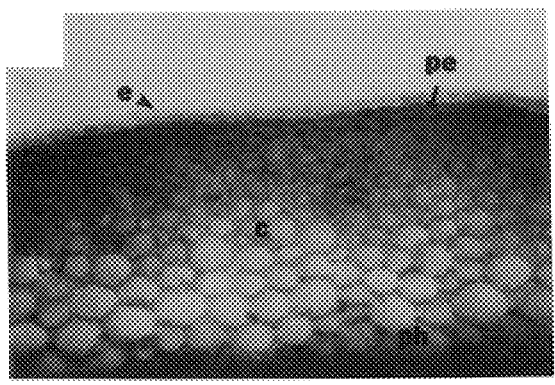

As shown in FIGS. 8B–F, GUS activity was present in elicitor-infiltrated zones of transgenic leaves, indicating that the EAS4 promoter (−1148 to +67) was activated in response to cryptogein or parasicein infiltration throughout the leaf tissue, except in the epidermal cell layers where minimal GUS activity was observed. A similar weak staining pattern was observed in root and stem epidermal cells (FIGS. 8G and 8L). While minimal GUS activity was found in the epidermal cells of the transgenic leaves, GUS activity was observed in trichomes of both the leaf and root of transgenic plants (FIGS. 8B and 8L).

Figure 8F:
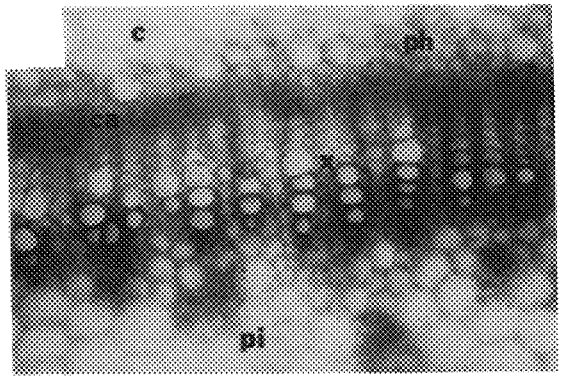
Figure 8G:
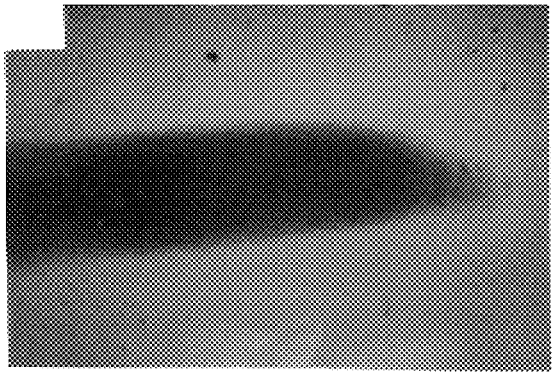
Figure 8H:
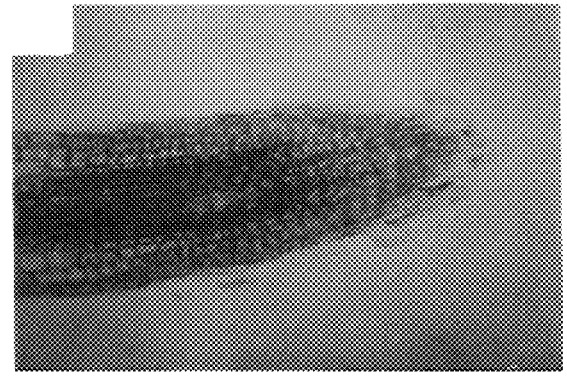
Figure 8I:
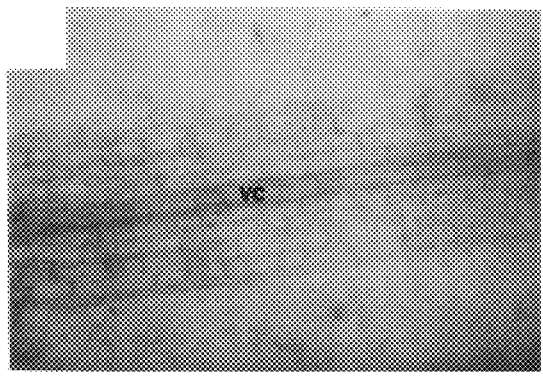
Figure 8J:
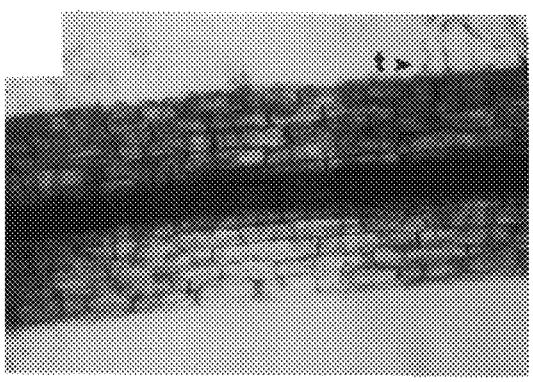
Figure 8K:
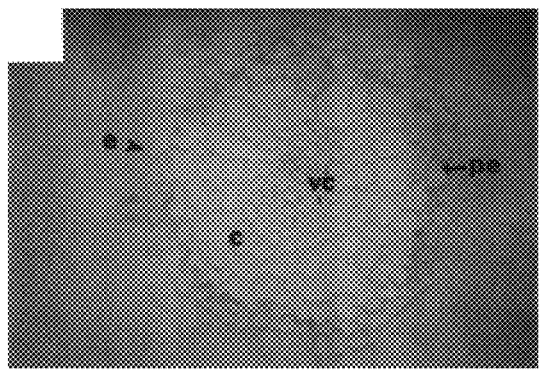
Figure 8L:
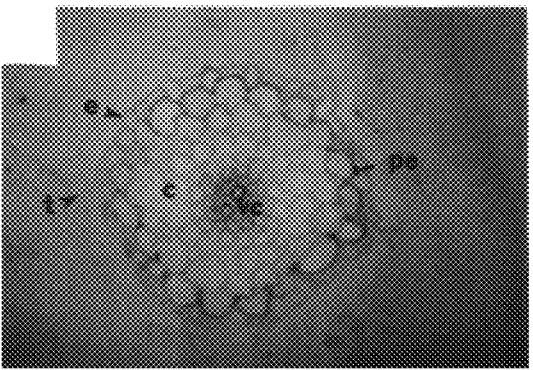

In addition, as shown in FIGS. 8C–F and FIG. 8L, elicitor-inducible GUS activity was observed in a distinct subepidermal layer of both stem and root sections (FIGS. 8C–F and 8L). FIG. 8F shows that GUS activity in stem tissue was also present in the cambial, phloem, and primary xylem tissue layers; minimal GUS activity was observed in cortical regions of the stem. Furthermore, like stem tissue, GUS activity was localized within the vascular system of the roots (FIG. 8L).

No GUS activity was observed in flower petals, including pigmented and non-pigmented tissue, either before and after treatment with cryptogein.

Example 14

5' Deletion Analysis of the EA84 Promoter (−1147 to +67) in Transgenic Tobacco Plants In another series of experiments, several 5' deletion constructs of the EAS4 promoter (−1147 to +67) were generated using standard PCR methodology. These promoter deletions were then fused to the GUS reporter gene in either pBI101.1 and pBI221 vectors and subsequently transformed into tobacco as described above.

TABLE 1

| | GUS Activity (MU/mg protein/min) | | | |
|---|---|---|---|---|
| 5' Deletions | Control (water-infiltrated) | Elicitor-treated | Fold Induction | # of independent transgenic lines tested |
| −1148 | 173 | 1889 | 10.9 | 11 |
| −567 | 120 | 921 | 7.7 | 12 |
| −212 | 23 | 187 | 8.1 | 11 |
| −160 | 2 | 34 | 17.0 | 9 |
| −115 | 3 | 3 | 1 | 12 |
| −63 | 0 | 0 | 0 | 13 |

As shown in Table 1, deleting the EAS4 promoter from −1148 to −567 decreased inducible GUS activity to 50% of the level of that found in plants with a full-length EAS4 promoter (−1148 to +67). Further deletion of the promoter to −212 decreased inducible GUS activity by an average of 90%, and deleting to −160 decreased GUS activity to 2% of that exhibited by plants having a full-length EAS4 promoter (−1148 to +67). Deletion to −63, a promoter which still contains putative CAAT and TATA boxes, completely abolished expression of the chimeric gene in control and elicitor-treated leaves. These data indicated that multiple positive regulatory elements which control the quantitative expression levels of EAS4 in tobacco are contained within the −1148 to −160 region.

Comparison of the results obtained with deletion to −567 and to −212 also indicated that the sequence within −567 to −212 contributed to the levels of expression, because deletion from −567 to −212 resulted in a 4-fold decrease in expression levels with a loss of large amounts of GUS activity. Although a deletion to −160 largely removed inducible GUS activity, the sequence downstream of −160 was found to be sufficient to direct inducible gene expression in leaf tissue. As shown in FIG. 9B, a 17-fold induction was observed in leaf tissues treated with elicitor. These data demonstrated that a qualitative element controlling the elicitor inducibility is located between −160 to −115.

Example 15

Disease-Resistant Transgenic Plants

The parA1 coding sequence was isolated from *Phytophthora parasitica* race 0 as follows: Genomic DNA was isolated and used as template in PCR with a SIG forward primer (CGTTGGATCCCCACCTCATCCGAAATGAAC; SEQ ID NO:9; BamHI site underlined); nucleotides 25–27 correspond to the translation start site and reverse primer (GGCTGAGCTCCTGGACGFCAGAGATCAAACC; SEQ ID NO:10; SstI site underlined) to amplify the coding region of the ParA1 elicitin including the signal peptide coding sequence. To isolate an amplimer corresponding to the coding sequence of the ParA1 elicitin, the MAT forward primer (GCCGGATCCTTATGACTAGTGCACCACCAC-GCAGCAAACTG, SEQ ID NO:11; BamHI site, GGATCC, and SpeI site, ACTAGT, underlined; translation start site at nucleotides 12–14) and the reverse primer as before (SEQ ID NO:10) were used with genomic DNA as template.

For subcloning into pBluescript (Stratagene, La Jolla, Calif.) or into pEAS4 constructs, the amplimer DNA was digested with BamHI and SstI. Where the mature protein's coding sequence is used, the mature elicitin/pEAS4 construct can be digested with SpeI to insert a plant signal sequence at the 5' end of the open reading frame. The pEAS4-GUS vector is digested with BamHI and SstI, with the large fragment of DNA being purified after agarose gel electrophoresis.

Figure 9:
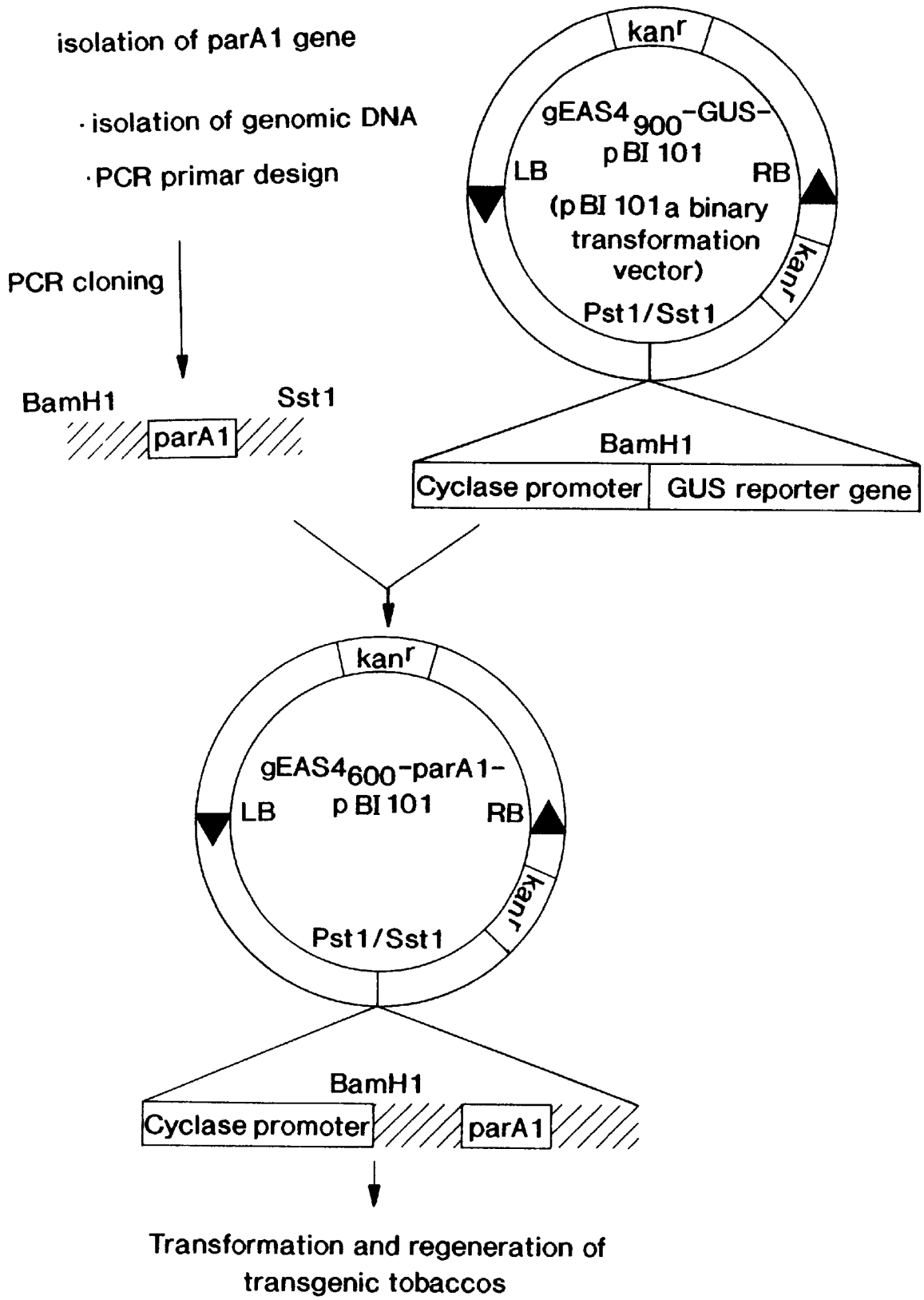
FIG. 9 is a schematic of the genetic manipulations leading to generation of disease-resistant plants. The coding sequence for the ParA1 elicitin is isolated by PCR so as to have BamHI and SstI ends. g 186:551–557; Huet et al. (1992) *Phytochemistry* 31:1471–1476; Huet and Pernollet (1992) *FEBS Lett.* 257:302–306; Kamoun et al. (1993) *Mol. Plant-Microbe Interact.* 5:22–33]. Several avirulent genes from pathogenic bacteria which correspond to elicitin activity have been characterized. For example, Keen, N. T. (1990) *Annu. Rev. Phytopathol.* 24:383–409 has described an avirulence gene of *Fulva fulvia*. Hammond-Kosack et al. (1994) *Proc. Natl. Acad. Sci. USA* 91:10445–10449 have described the avr gene of *Cladosporium fulvum*, which functions in the same way as the *P. parasitica* elicitin.

FIG. 9 illustrates the molecular manipulations leading to the generation of disease-resistant plants. The coding sequence for the ParA1 elicitin is isolated by PCR so as to have BamHI and SstI ends. gEAS4$_{600(cyclase)}$-GUS-pBI101, which directs the expression of the GUS reporter gene under the regulatory control of the EAS promoter, is digested with BamHI and SstI to release the GUS reporter gene. Then the BamHI/SstI-digested parA1 amplimer is ligated to the large fragment produced after digestion of gEAS4$_{600(cyclase)}$-GUS-pBI101 to produce gEAS4$_{600(cyclase)}$-parA1 -pBI101, from which the ParA1 elicitin is synthesized following induction with a suitable elicitor once plant cells or tissue have been transformed.

To assess resistance to plant pathogens, transgenic tobacco plants (*Nicotiana tabacum* cv. KY160) containing either the parA1 mature elicitin gene (amino acids 21–118 of SEQ ID NO: 12) or parA1 elicitin-with-signal sequence gene (amino acids 1–118 of SEQ ID NO: 12) under the control of the gEAS4$_{600(cyclase)}$ promoter were regenerated using the Agrobacterium-mediated gene transfer technique as described above. The resulting transgenic plants were then tested for disease resistance against either race 0 or race 1 isolates of *Phythopthora parasitica* var. Nicotianae using the standard detached leaf assay described by Tedford et al. (supra).

Figure 10:
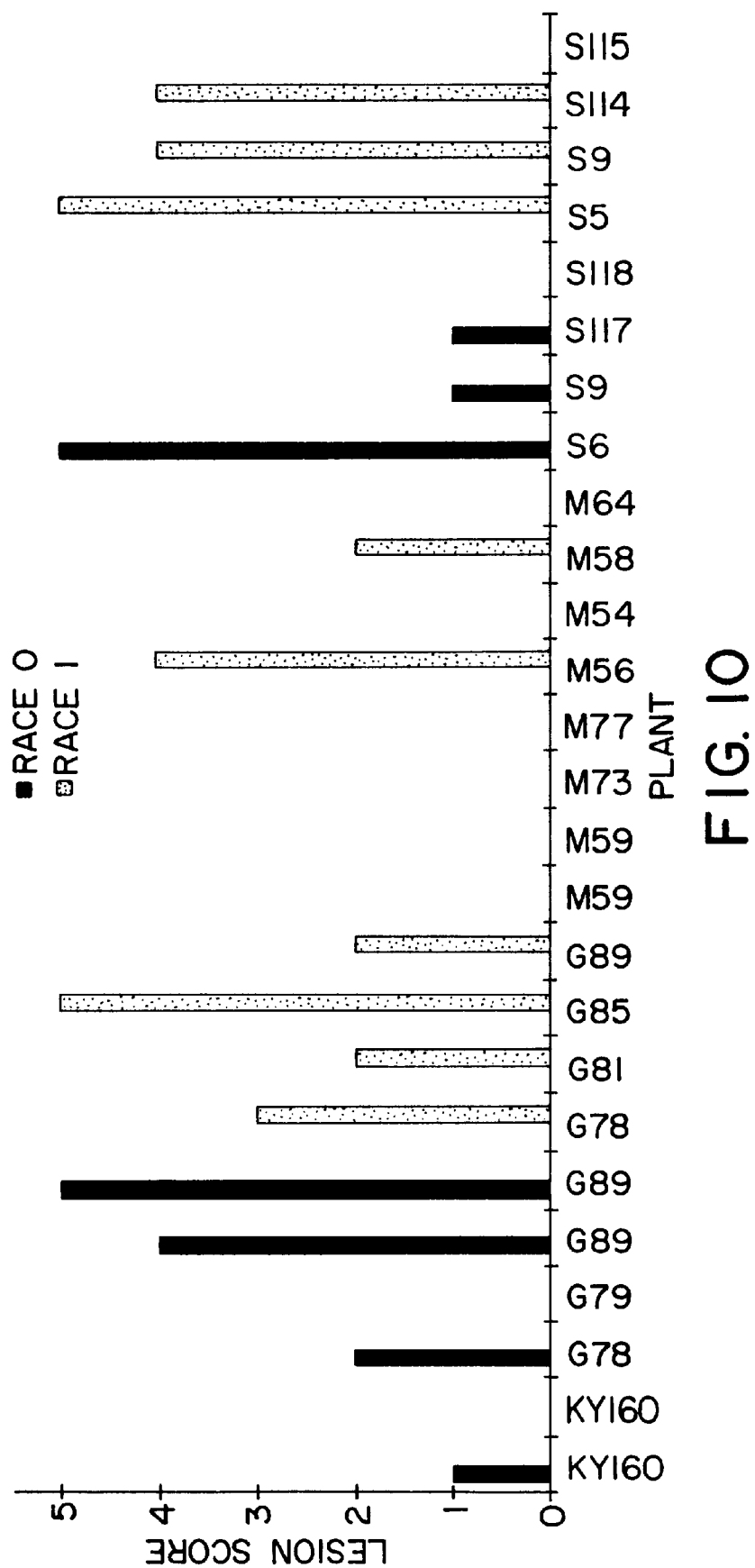

As shown in FIG. 10, several independent lines of transgenic tobacco containing the parA1 mature elicitin gene under the control of the gEAS4$_{600(cyclase)}$ promoter showed enhanced disease resistance to both race 0 and race 1 of P. p. var. Nicotianae relative to control plants (that is, relative to non-transformed *N. tabacum* cv. KY160 or transgenic *N. tabacum* cv. KY160 containing the EAS4600(cyclase) promoter: GUS reporter gene).

While various embodiments of the present invention have been described in detail, it is apparent that modifications, extensions, adaptations and optimizations may occur to those skilled in the art. It is to be expressly understood that such modifications and adaptations and so on are within the spirit and scope of the present invention, as set forth in the claims.

What is claimed is:

1. A recombinant nucleic acid molecule comprising a pathogen- or elicitor-inducible transcriptional regulatory element comprising nucleotides 463–473 of SEQ ID NO:2, nucleotides 406 to 486 of SEQ ID NO:2, nucleotides 463 to 572 of SEQ ID NO:2, nucleotides 371 to 463 of SEQ ID NO:2, or nucleotides 411 to 457 of SEQ ID NO:2.

2. The nucleic acid molecule of claim 1, wherein said transcriptional regulatory element is obtained from a gene encoding a terpene cyclase.

3. The nucleic acid molecule of claim 2, wherein said terpene cyclase is a sesquiterpene cyclase.

4. The nucleic acid molecule of claim 3, wherein said transcriptional regulatory element directs expression of an epi-5-aristolochene synthase (EAS).

5. The nucleic acid molecule of claim 4, said nucleic acid molecule comprising the nucleotide sequence shown in FIG. 3A (SEQ ID NO:14) or a pathogen- or elicitor-inducible fragment thereof.

6. The nucleic acid molecule of claim 5, wherein said nucleic acid molecule has the nucleotide sequence shown in FIG. 3A (SEQ ID NO: 14).

7. The nucleic acid molecule of claim 1, wherein said transcriptional regulatory element is obtained from a dicot.

8. The nucleic acid molecule of claim 7, wherein said dicot is a member of the Solanaceae.

9. The nucleic acid molecule of claim 8, wherein said Solanaceous plant is a member of the genus Nicotiana.

10. The nucleic acid molecule of claim 1, wherein said transcriptional regulatory element is obtained from a monocot.

11. The nucleic acid molecule of claim 1, wherein said transcriptional regulatory element is obtained from a gymnosperm.

12. The nucleic acid molecule of claim 1, wherein said transcriptional regulatory element is obtained from a conifer.

13. The nucleic acid molecule of claim 1, wherein said transcriptional regulatory element is genomic DNA.

14. The nucleic acid molecule of claim 1, wherein said transcriptional regulatory element is chemically-sythesized DNA.

15. The nucleic acid molecule of claim 1, wherein said transcriptional regulatory element is a combination of genomic DNA and chemically-synthesized DNA.

16. The nucleic acid molecule of claim 1, wherein said nucleic acid molecule is a combination of genomic DNA and cDNA or a combination of genomic DNA, cDNA, and chemically-synthesized DNA.

17. The nucleic acid molecule of claim 1, wherein said transcriptional regulatory element increases downstream gene expression in plant tissue in response to an elicitor or a plant pathogen.

18. The nucleic acid molecule of claim 17, wherein said plant pathogen is a fungus.

19. The nucleic acid molecule of claim 18, wherein said fungus is a member of the genus Phytophthora.

20. The nucleic acid molecule of claim 17, wherein said plant pathogen is a bacterium.

21. The nucleic acid molecule of claim 20, wherein said bacterium is a member of the genus Pseudomonas.

22. The nucleic acid molecule of claim 17, wherein said plant pathogen is a virus.

23. The nucleic acid molecule of claim 22, wherein said virus is tobacco mosaic virus.

24. The nucleic acid molecule of claim 1, wherein said transcriptional regulatory element is induced by an elicitor.

25. The nucleic acid molecule of claim 17, wherein said elicitor is a fungal elicitor.

26. The nucleic acid molecule of claim 17, wherein said elicitor is a bacterial elicitor.

27. The nucleic acid molecule of claim 1, wherein said nucleic acid molecule is operably linked to nucleotide sequences encoding a heterologous polypeptide.

28. The nucleic acid molecule of claim 27, wherein said heterologous polypeptide is capable of conferring disease-resistance to a plant.

29. The nucleic acid molecule of claim 28, wherein said heterologous polypeptide is an elicitin.

30. The nucleic acid molecule of claim 28, wherein said elicitin is a fungal elicitin.

31. The nucleic acid molecule of claim 30, said fungal elicitin being from Phytophthora.

32. The nucleic acid molecule of claim 31, said elicitin comprising a ParA1 polypeptide.

33. The nucleic acid molecule of claim 29, wherein said elicitin is a bacterial elicitin.

34. The nucleic acid molecule of claim 33, wherein said bacterial elicitin is a harpin.

35. The nucleic acid molecule of claim 27, wherein the expression of said heterologous polypeptide is mediated by one or more external agents.

36. The nucleic acid molecule of claim 27, wherein said nucleic acid molecule expresses said heterologous polypeptide in a cell-specific manner.

37. The nucleic acid molecule of claim 27, wherein said heterologous polypeptide is a pharmaceutical protein.

38. A vector comprising the DNA of claim 1.

39. The vector of claim 38, wherein said vector inducibly expresses a nucleotide sequence in a cell comprising said vector.

40. The vector of claim 39, said nucleotide sequence coding for a heterologous polypeptide.

41. A transgenic plant comprising the nucleic acid molecule of claim 1 integrated into the genome of said plant.

42. A transgenic plant comprising the nucleic acid molecule of claim 27 integrated into the genome of said plant.

43. A seed from the transgenic plant of claim 41.

44. A seed from the transgenic plant of claim 42.

45. A cell from the transgenic plant of claim 41.

46. A cell from the transgenic plant of claim 42.

47. A method of providing disease-resistance to a transgenic plant, said method comprising the steps of:
  (a) producing a transgenic plant cell comprising the nucleic acid molecule of claim 28 integrated into the genome of said transgenic plant cell; and
  (b) regenerating said transgenic plant from said plant cell wherein the expression of said nucleic acid molecule of claim 28 confers disease-resistance to said transgenic plant.

48. The method of claim 47, wherein said transgenic plant is a dicot.

49. The method of claim 48, wherein said dicot is a member of the Solanaceae.

50. The method of claim 49, wherein said member of the Solanaceae is a member of the genus Nicotiana.

51. The method of claim 47, wherein said transgenic plant is a monocot.

52. The method of claim 47, wherein said transgenic plant is a gymnosperm.

53. The method of claim 47, wherein said transgenic plant is a conifer.

54. A method of increasing the transcriptional expression of a downstream DNA sequence in a transgenic plant cell, said method comprising the steps of:
  (a) producing a transgenic plant cell comprising the nucleic acid molecule of claim 1 positioned for increasing transcription of a downstream DNA sequence and integrated into the genome of said transgenic plant cell; and
  (b) regenerating said transgenic plant from said plant cell.

* * * * *

UNITED STATES PATENT AND TRADEMARK OFFICE
CERTIFICATE OF CORRECTION

PATENT NO. : 6,100,451
DATED : August 8, 2000
INVENTOR(S) : Chappell et al.

It is certified that error appears in the above-identified patent and that said Letters Patent is hereby corrected as shown below:

<u>Title page,</u>
Item [56], OTHER PUBLICATIONS,
Delete duplicate entries for Bonnet et al. (1994);
Delete duplicate entries for Gough et al. (1995);
Delete duplicate entries for Huang et al. (1994);

<u>Column 5,</u>
Line 12, replace "a combat" with -- combat a --;

<u>Column 10,</u>
Line 64, replace "573-14 581" with -- 573-581 --;

<u>Column 15,</u>
Line 27, replace "Xanthominas" with -- Xanthomonas --;

<u>Column 16,</u>
Line 19, replace "BiolTechnology" with -- Bio/Technology --;
Line 21, replace "BiolTechnology" with -- Bio/Technology --;

<u>Column 20,</u>
Line 13, replace "PBSK" with -- pBSK --;

<u>Column 25,</u>
Line 34, replace "EAS5" with -- EAS4 5' --;

<u>Column 27,</u>
Line 64, replace "GU8" with -- GUS --;

UNITED STATES PATENT AND TRADEMARK OFFICE
CERTIFICATE OF CORRECTION

PATENT NO. : 6,100,451
DATED : August 8, 2000
INVENTOR(S) : Chappell et al.

It is certified that error appears in the above-identified patent and that said Letters Patent is hereby corrected as shown below:

Column 28,
Line 40, replace "EA84" with -- EAS4 --;

Column 30,
Line 36, replace "EAS4600 (cyclase)" with -- $EAS4_{600(cyclase)}$ --.

Signed and Sealed this

First Day of April, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 512 base pairs
      (B) TYPE: nucleic acid
      (C) STRANDEDNESS: double
      (D) TOPOLOGY: linear (ii) MOLECULE TYPE: DNA (iii) HYPOTHETICAL: NO (iv) ANTI-SENSE: NO (vi) ORIGINAL SOURCE:
            (A) ORGANISM: Nicotiana tabacum (xi) SEQUENCE DESCRIPTION: SEQ ID NO:1:

| | | | | | |
|---|---|---|---|---|---|
| CCGCGATTGG | AGGATGTTGT | ACGTCGAGCT | ACGCGGCACC | GCGCTTAATT | TTACTCGGTC | 60 |
| AAGAAGGAAC | GGGGATGGTG | GTCAACGAAA | CACGACGGGC | CCGACATCAT | GCCTGACAAC | 120 |
| CCGCCGTGGG | TGAAGAAGTC | GACGTTGGAA | AAGAGCTACA | GCCTGCTCCA | CGCGGATGCG | 180 |
| GGGATGGCCG | CTGACTACAG | AAAGTGCGTT | TCCCGCCACC | CGGGGCGAGC | CCGGGTTTTG | 240 |
| AAGATCAATG | CTGACCGAAC | CAGACGGCGG | TACGTCATCC | GCTTGAGGGT | AGAGACGGAT | 300 |
| CAGTTCTTGT | TGTCGTGTGT | CGAACTCGGG | ACGTTTGTCA | CATGGCTGGA | CGGGTTATTC | 360 |
| GCCGCCATCA | ACGTGTCGCC | GCCAATCGAC | GAGCGCGACT | TCCCAGAGA | CTTTAGCGTG | 420 |
| CCACGGATCA | ATTACATTAA | CTAGTCTCTC | ACCACTATAT | ATACTTGTCC | CTTCTCTTCC | 480 |
| ATTTAAGTAG | AGTTCCTTTC | TTTCTTCCTT | AA | | | 512 |

(2) INFORMATION FOR SEQ ID NO:2:

(i) SEQUENCE CHARACTERISTICS:
        (A) LENGTH: 642 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Nicotiana tabacum (xi) SEQUENCE DESCRIPTION: SEQ ID NO:2:

| | | | | | |
|---|---|---|---|---|---|
| TAGGTGAATG | TCAGGGCTTA | TGCTCCACGA | TACTTATGCC | CTGCCAGTAC | ACCTCGCGGT | 60 |
| GGGACTCGCT | CAAAAAACGT | CTTTGTTGTG | AGAAATTGCA | ATTTTGAACC | TCTACAATTT | 120 |
| CGACAAAACC | TTGGTTCGTG | AAAACTGTTT | GATTAACTTT | TAGACCATCC | AGTCAATTTA | 180 |
| ACTCTAAACT | GACCTAAATA | AATACTACGT | ACACTAGTCT | TTAAGTTCAT | CAAAGTGGAC | 240 |
| TCTGCATTAA | TAATTGAAAT | TTATGCCGCA | ACAATGACAT | TAGGTTTTAT | AAATAAAGTA | 300 |
| ATAGGAATTT | GATAGTTCCA | GGAAACAACT | CTACAGTACT | CCCTTATTTT | GTGCCTTTTT | 360 |
| AAATAATATT | ATTCAGTTGA | CGAAACAAAT | AAATAAAATA | TTTGGGAAAC | TGGATCAATA | 420 |
| GACCCCAGAC | GCCAACAATG | AATCAAAAGG | CTGCTAGCTA | GTGTAAAGTC | TAGTAAGGCA | 480 |
| ACTGGGAAAT | TAAATGATTA | GGTGCTTTTG | ATCAATTACA | TTAACTAGTC | TCTCACCACT | 540 |
| ATATATACTT | GTCCCTTCTC | TTCCATTTAA | GTAGAGTTCC | TTTCTTTCTT | CCTTAAAACT | 600 |
| TAAAAGAACA | AGTAAAAATA | CACTCATCTT | TAATTAGCAA | TG | | 642 |

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR"

(iii) HYPOTHETICAL: NO (iv) ANTI-SENSE: NO (xi) SEQUENCE DESCRIPTION: SEQ ID NO:3:

ATGCTGTTAG CAACCGGAAG G                                                      21

(2) INFORMATION FOR SEQ ID NO:4:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Oligonucleotide primer for
                    PCR"

(iii) HYPOTHETICAL: NO (iv) ANTI-SENSE: YES (xi) SEQUENCE DESCRIPTION: SEQ ID NO:4:

ATCCAAAATC TCATCAATTT C                                                      21

(2) INFORMATION FOR SEQ ID NO:5:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Oligonucleotide primer for
                    PCR."

(iii) HYPOTHETICAL: NO (iv) ANTI-SENSE: YES (xi) SEQUENCE DESCRIPTION: SEQ ID NO:5:

ATGAGTCCTT ACATGTGA                                                          18

(2) INFORMATION FOR SEQ ID NO:6:

(i) SEQUENCE CHARACTERISTICS:
                (A) LENGTH: 45 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "Oligonucleotide primer for
                    PCR."

(iii) HYPOTHETICAL: NO (iv) ANTI-SENSE: YES (xi) SEQUENCE DESCRIPTION: SEQ ID NO:6:

GGGAGCTCGA ATTCCATGGC CTCAGCAGCA GCAGTTGCAA ACTAT                            45

(2) INFORMATION FOR SEQ ID NO:7:

(i) SEQUENCE CHARACTERISTICS:
                (A) LENGTH: 4253 base pairs
                (B) TYPE: nucleic acid
                (C) STRANDEDNESS: double
                (D) TOPOLOGY: linear (ii) MOLECULE TYPE: DNA

```
      (iii) HYPOTHETICAL: NO (iv) ANTI-SENSE: NO (vi) ORIGINAL SOURCE:
            (A) ORGANISM: Nicotiana tabacum (ix) FEATURE:
            (A) NAME/KEY: CDS
            (B) LOCATION: 1216..1327

(ix) FEATURE:
            (A) NAME/KEY: CDS
            (B) LOCATION: 1454..1718

(ix) FEATURE:
            (A) NAME/KEY: CDS
            (B) LOCATION: 1805..2182

(ix) FEATURE:
            (A) NAME/KEY: CDS
            (B) LOCATION: 2259..2477

(ix) FEATURE:
            (A) NAME/KEY: CDS
            (B) LOCATION: 2609..2747

(ix) FEATURE:
            (A) NAME/KEY: CDS
            (B) LOCATION: 2902..3148

(ix) FEATURE:
            (A) NAME/KEY: CDS
            (B) LOCATION: 3261..3555

(xi) SEQUENCE DESCRIPTION: SEQ ID NO:7:

AAGCTTTACG AATTAGATGT AAAAAGACGC AAACTACTTA TATATATTAC CAAAGTAACT      60

TGAAAGTTTA AAATTTCAAT TAGAACTATA GTAGGGTAAA ACTGTCTATT TAAAATCAGT     120

ATTTAAAAAG GCATGAGCGA AGATGAGGC GTTTTATCTA ACACGAAGCG AGGTGTAAGC     180

CCCATGGTGT TTTATTTTTA TATTTTATAA ATTTATAAAA TCATTATATA AATCAGAAAA     240

ATACACTAAA ATTGTGAAAA GTTAAAGAAA ATTATAGAAT TAATATATAT ATATATATAT     300

ATATATATAT ATATATATAT ATATATATAT ATATATATAA ATGTATGTGT GTGTGTGTGT     360

GTATCGCATG CGCGCGACCA TGCAACTTTT TTTTCTTGAA AAAATAAAAG GCGTAAAGAT     420

ACATTATACC TATGTCATCA AAACAATATA AAAACTAGAG CGATACCAAA GGAAATTTTA     480

AATTCAAAAA CTAACTTGAA ATTAATATAT TTAAAATTTC ATTTTTTTTT GTGTGGAGAA     540

AACAAAGCAT AACACTTTGC TTTGTAACAC TTTGCCTAGG TGAATGTCAG GCTTATGCT      600

CCACGATACT TATGCCCTGC CAGTACACCT CGCAGTGGGA CTCGCTGAAA AAACGTCTTT     660

GTTGTGAGAA ATTGCAATTT TGAACCTCTA CAATTTCGAC AAAACCTTGG TTCGTGAAAA     720

CTGTTTGATT AACTTTTAGA CCATCCAGTC AATTTAACTC TAAACTGACC TAAATAAATA     780

CTACGTACAC TAGTCTTTAA GTTCATCAAA GTGGACTCTG CATTAATAAT TGAAATTTAT     840

GCCGCAACAA TGACATTAGG TTTTATAAAT AAAGTAATAG GAATTTGATA GTTCCAGGAA     900

ACAACTCTAC AGTACTCCCT TATTTTGTGC CTTTTTAAAT AATATTATTC AGTTGACGAA     960

ACAAATAAAT AAAATATTTG GGAAACTGGA TCAATAGACC CCAGACGCCA ACAATGAATC    1020

AAAAGGCTGC TAGCTAGTGT AAAGTCTAGT AAGGCAACTG GGAAATTAAA TGATTAGGTG    1080

CTTTTGATCA ATTACATTAA CTAGTCTCTC ACCACTATAT ATACTTGTCC CTTCTCTTCC    1140

ATTTAAGTAG AGTTCCTTTC TTTCTTCCTT AAAACTTAAA AGAACAAGTA AAAATACACT    1200
```

```
CATCTTTAAT TAGCA ATG GCC TCA GCA GCA GTT GCA AAC TAT GAA GAA GAG      1251
               Met Ala Ser Ala Ala Val Ala Asn Tyr Glu Glu Glu
               1               5                   10

ATT GTT CGC CCC GTC GCC GAC TTC TCC CCT AGT CTC TGG GGT GAT CAG       1299
Ile Val Arg Pro Val Ala Asp Phe Ser Pro Ser Leu Trp Gly Asp Gln
        15                  20                  25

TTC CTT TCA TTC TCC ATT GAT AAT CAG G TAATTTAACT AATACTAGTA           1347
Phe Leu Ser Phe Ser Ile Asp Asn Gln
        30                  35

TTCTTTATTT ATATTTATAG TTTGTTCTCC ATTGATAATC AGGTAGTTTA TTTATGTTGA     1407

ACAACATTAA TTTTGCTAAT TTCAGTTTAA TGTACATTAC ATATAG GTT GCG GAA        1462
                                                  Val Ala Glu
                                                  1

AAG TAT ATA TAT GCT CAA GAG ATT GAA GCA TTG AAG GAA CAA ACG AGG       1510
Lys Tyr Ile Tyr Ala Gln Glu Ile Glu Ala Leu Lys Glu Gln Thr Arg
        5                   10                  15

AGT ATG CTG TTA GCA ACC GGA AGG AAA TTG GCC GAT ACA TTG AAT TTG       1558
Ser Met Leu Leu Ala Thr Gly Arg Lys Leu Ala Asp Thr Leu Asn Leu
20                  25                  30                  35

ATT GAC ATT ATT GAA CGC CTT GGT ATA TCC TAC CAC TTT GAG AAA GAA       1606
Ile Asp Ile Ile Glu Arg Leu Gly Ile Ser Tyr His Phe Glu Lys Glu
                40                  45                  50

ATT GAT GAG ATT TTG GAT CAG ATT TAC AAC CAA AAC TCA AAC TGC AAT       1654
Ile Asp Glu Ile Leu Asp Gln Ile Tyr Asn Gln Asn Ser Asn Cys Asn
                    55                  60                  65

GAT TTG TGC ACC TCT GCA CTT CAA TTT CGA TTG CTC AGG CAA CAC GGT       1702
Asp Leu Cys Thr Ser Ala Leu Gln Phe Arg Leu Leu Arg Gln His Gly
            70                  75                  80

TTC AAC ATC TCT CCT G GTAAGTTCAT CATGAAGTTG TTAAAATTAT                1748
Phe Asn Ile Ser Pro
            85

TATCCATTTA TTGGAAGAAG GCTAATTCAT CTTGAGTTTT CTTTCTTGAA ATACCA         1804

GAA ATT TTC AGC AAA TTC CAA GAT GAA AAT GGC AAA TTC AAG GAG TCT       1852
Glu Ile Phe Ser Lys Phe Gln Asp Glu Asn Gly Lys Phe Lys Glu Ser
1               5                   10                  15

CTT GCT AGT GAT GTC TTA GGA TTA TTA AAC TTG TAT GAA GCT TCA CAT       1900
Leu Ala Ser Asp Val Leu Gly Leu Leu Asn Leu Tyr Glu Ala Ser His
            20                  25                  30

GTA AGG ACT CAT GCT GAC GAT ATC TTA GAA GAC GCA CTT GCT TTC TCC       1948
Val Arg Thr His Ala Asp Asp Ile Leu Glu Asp Ala Leu Ala Phe Ser
        35                  40                  45

ACT ATC CAT CTT GAA TCT GCA GCT CCA CAT TTG AAA TCT CCA CTT AGG       1996
Thr Ile His Leu Glu Ser Ala Ala Pro His Leu Lys Ser Pro Leu Arg
    50                  55                  60

GAG CAA GTG ACA CAT GCC CTT GAG CAA TGT TTG CAC AAG GGT GTT CCT       2044
Glu Gln Val Thr His Ala Leu Glu Gln Cys Leu His Lys Gly Val Pro
65                  70                  75                  80

AGA GTC GAG ACC CGA TTC TTC ATC TCA TCA ATC TAT GAC AAG GAA CAA       2092
Arg Val Glu Thr Arg Phe Phe Ile Ser Ser Ile Tyr Asp Lys Glu Gln
                85                  90                  95

TCG AAG AAT AAT GTG TTA CTT CGA TTT GCC AAA TTG GAT TTC AAC TTG       2140
Ser Lys Asn Asn Val Leu Leu Arg Phe Ala Lys Leu Asp Phe Asn Leu
                100                 105                 110

CTC CAG ATG TTG CAC AAA CAA GAA CTT GCT CAA GTA TCA AGG               2182
Leu Gln Met Leu His Lys Gln Glu Leu Ala Gln Val Ser Arg
            115                 120                 125

TGCGATATAT AAAAACGATG AACCCTTTTT GATTCATCAT ATCTCAAGTA CTCATGTTAA     2242
```

```
TTTCTTATGC TGCAGG TGG TGG AAA GAT TTG GAT TTT GTA ACA ACA CTT        2291
               Trp Trp Lys Asp Leu Asp Phe Val Thr Thr Leu
                 1               5                  10

CCA TAT GCT AGA GAT CGA GTA GTT GAA TGC TAC TTT TGG GCA TTA GGA      2339
Pro Tyr Ala Arg Asp Arg Val Val Glu Cys Tyr Phe Trp Ala Leu Gly
             15                  20                  25

GTT TAT TTT GAG CCT CAA TAC TCT CAA GCT CGC GTC ATG CTC GTT AAG      2387
Val Tyr Phe Glu Pro Gln Tyr Ser Gln Ala Arg Val Met Leu Val Lys
         30                  35                  40

ACC ATA TCA ATG ATT TCG ATT GTC GAT GAC ACC TTT GAT GCT TAC GGT      2435
Thr Ile Ser Met Ile Ser Ile Val Asp Asp Thr Phe Asp Ala Tyr Gly
             45                  50                  55

ACA GTT AAA GAA CTT GAG GCA TAC ACA GAT GCC ATA CAA AGG              2477
Thr Val Lys Glu Leu Glu Ala Tyr Thr Asp Ala Ile Gln Arg
 60                  65                  70

TATGAACTTC ATCAATTCAC TTATTCCTTG ATAGTGAATG TCGTCGTGAA AAGATTAAGA    2537

CGAATTTCTA CTCATTATAG TTGTGCTCTT TCAAAATGCA TGAATTCACC TTAATTTTGT    2597

CATCCTGCAG A TGG GAT ATC AAC GAA ATT GAT CGG CTT CCT GAT TAC ATG     2647
             Trp Asp Ile Asn Glu Ile Asp Arg Leu Pro Asp Tyr Met
              1               5                  10

AAA ATC AGT TAT AAA GCT ATT CTA GAT CTC TAC AAG GAT TAT GAA AAG      2695
Lys Ile Ser Tyr Lys Ala Ile Leu Asp Leu Tyr Lys Asp Tyr Glu Lys
             15                  20                  25

GAA TTG TCT AGT GCC GGA AGA TCT CAT ATT GTC TGC CAT GCA ATA GAA      2743
Glu Leu Ser Ser Ala Gly Arg Ser His Ile Val Cys His Ala Ile Glu
         30                  35                  40                  45

AGA G TATGTTCGAG CAACTTAACT ATCGAAATAC ATTTTTTCCT TAATCCATTT         2797
Arg

CTCACTTTGG TTTACCTTGT GTTCGTCTTT TAGTGATTAG AAACTTGATA CAGTTCAATC    2857

AATATTTTCT AACACTTGAA CACATATATG TTTTGTATTC ACAG ATG AAA GAA GTA     2913
                                                Met Lys Glu Val
                                                 1

GTA AGA AAT TAT AAT GTC GAG TCA ACA TGG TTT ATT GAA GGA TAT ATG      2961
Val Arg Asn Tyr Asn Val Glu Ser Thr Trp Phe Ile Glu Gly Tyr Met
 5                  10                  15                  20

CCA CCT GTT TCT GAA TAC CTA AGC AAT GCA CTA GCA ACT ACC ACA TAT      3009
Pro Pro Val Ser Glu Tyr Leu Ser Asn Ala Leu Ala Thr Thr Thr Tyr
             25                  30                  35

TAC TAC CTC GCG ACA ACA TCG TAT TTG GGC ATG AAG TCT GCC ACG GAG      3057
Tyr Tyr Leu Ala Thr Thr Ser Tyr Leu Gly Met Lys Ser Ala Thr Glu
             40                  45                  50

CAA GAT TTT GAG TGG TTG TCA AAG AAT CCA AAA ATT CTT GAA GCT AGT      3105
Gln Asp Phe Glu Trp Leu Ser Lys Asn Pro Lys Ile Leu Glu Ala Ser
         55                  60                  65

GTA ATT ATA TGT CGA GTT ATC GAT GAC ACA GCC ACG TAC GAG G            3148
Val Ile Ile Cys Arg Val Ile Asp Asp Thr Ala Thr Tyr Glu
 70                  75                  80

TATGATTTGC ATCTCAAGAA ATTATATCAT TATATGGGAT TTGGACAAAC AAAGTGTTGC    3208

GACGACAATT AAGGCAATAT AAAAGCTAAC CTTTAATTTA TCTGCTTTCT AG GTT        3263
                                                         Val
                                                          1

GAG AAA AGC AGG GGA CAA ATT GCA ACT GGA ATT GAG TGC TGC ATG AGA      3311
Glu Lys Ser Arg Gly Gln Ile Ala Thr Gly Ile Glu Cys Cys Met Arg
             5                   10                  15

GAT TAT GGT ATA TCA ACA AAA GAG GCA ATG GCT AAA TTT CAA AAT ATG      3359
Asp Tyr Gly Ile Ser Thr Lys Glu Ala Met Ala Lys Phe Gln Asn Met
             20                  25                  30
```

```
GCT GAG ACA GCA TGG AAA GAT ATT AAT GAA GGA CTT CTT AGG CCC ACT          3407
Ala Glu Thr Ala Trp Lys Asp Ile Asn Glu Gly Leu Leu Arg Pro Thr
         35                  40                  45

CCC GTC TCT ACA GAA TTT TTA ACT CCT ATT CTC AAT CTT GCT CGT ATT          3455
Pro Val Ser Thr Glu Phe Leu Thr Pro Ile Leu Asn Leu Ala Arg Ile
 50                  55                  60                  65

GTT GAG GTT ACA TAT ATA CAC AAT CTA GAT GGA TAC ACT CAT CCG GAG          3503
Val Glu Val Thr Tyr Ile His Asn Leu Asp Gly Tyr Thr His Pro Glu
                 70                  75                  80

AAA GTC TTA AAA CCT CAC ATT ATT AAC CTA CTT GTG GAC TCC ATC AAA          3551
Lys Val Leu Lys Pro His Ile Ile Asn Leu Leu Val Asp Ser Ile Lys
                     85                  90                  95

ATT T GAGCTGCCAT TGTTGCTCA TCTCAAGGAA ACTTCATTCT TCTTTGTGCA              3605
Ile

GTTGTGCAGT AGACTTCCTA ACTAGGAGCT TCTTAAGATC CTTGTAAGAA ATAATCTTCA         3665

AGTGTTATGA ATCCGCATTG TGGAGAAATC TTTTTATATG ACAATAAGTT ATGTTATGAA         3725

GAATGTTATG GGGGTCTCTT ATGACCTATT TGTCAGTGTA TGAAGTAATC TGAGCCTGTC         3785

GAAAAAAAG GTAATCTGAG CCTTTTGCTC GTCCTTCCTT TAGTATTTCT TTTTATCATA          3845

CTTGGTCTCA CAAAAATTAG TTTTTGGCAC CTTTGTTTTT CCTTGTGGCG CATGTGTATA         3905

TACATCTGAA ACATATACTT AAAGGTTAAG AGGACATTGA CATATTGAAT CAACACTAGT         3965

GTTATTGGCA TACAGGAGAG AATCTATGTG TAAAGGACGG GGTGGAACCC CACCCACAAG         4025

ACTTGGTCGA GACTATTGTT TATCGAAAAA ACGGTACAGT TGAATTTATA CGTGGTTTAT         4085

AGACAAGTGA ATTAATTTGA TCCTAAAATA ATAGGCGAAT TAGATAAAAA TGTAATTCTT         4145

AGCCTTGAGT TGGAGACGAA ATAGCAGAAA TAGTGATTCC AGGAGAAAGG CTTTCGGGTA         4205

CCACAACAAT GATATCAAAA AATAAAAAGA TAAAATTGTA TTAAGCTT                     4253

(2) INFORMATION FOR SEQ ID NO:8:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Ser Ala Ala Val Ala Asn Tyr Glu Glu Glu Ile Val Arg Pro
 1               5                  10                  15

Val Ala Asp Phe Ser Pro Ser Leu Trp Gly Asp Gln Phe Leu Ser Phe
                 20                  25                  30

Ser Ile Asp Asn Gln Val Ala Glu Lys Tyr Ile Tyr Ala Gln Glu Ile
         35                  40                  45

Glu Ala Leu Lys Glu Gln Thr Arg Ser Met Leu Leu Ala Thr Gly Arg
 50                  55                  60

Lys Leu Ala Asp Thr Leu Asn Leu Ile Asp Ile Ile Glu Arg Leu Gly
 65                  70                  75                  80

Ile Ser Tyr His Phe Glu Lys Glu Ile Asp Glu Ile Leu Asp Gln Ile
                     85                  90                  95

Tyr Asn Gln Asn Ser Asn Cys Asn Asp Leu Cys Thr Ser Ala Leu Gln
                100                 105                 110

Phe Arg Leu Leu Arg Gln His Gly Phe Asn Ile Ser Pro Glu Ile Phe
            115                 120                 125

Ser Lys Phe Gln Asp Glu Asn Gly Lys Phe Lys Glu Ser Leu Ala Ser
        130                 135                 140
```

```
Asp Val Leu Gly Leu Leu Asn Leu Tyr Glu Ala Ser His Val Arg Thr
145                 150                 155                 160

His Ala Asp Asp Ile Leu Glu Asp Ala Leu Ala Phe Ser Thr Ile His
            165                 170                 175

Leu Glu Ser Ala Ala Pro His Leu Lys Ser Pro Leu Arg Glu Gln Val
                180                 185                 190

Thr His Ala Leu Glu Gln Cys Leu His Lys Gly Val Pro Arg Val Glu
        195                 200                 205

Thr Arg Phe Phe Ile Ser Ser Ile Tyr Asp Lys Glu Gln Ser Lys Asn
    210                 215                 220

Asn Val Leu Leu Arg Phe Ala Lys Leu Asp Phe Asn Leu Leu Gln Met
225                 230                 235                 240

Leu His Lys Gln Glu Leu Ala Gln Val Ser Arg Trp Trp Lys Asp Leu
            245                 250                 255

Asp Phe Val Thr Thr Leu Pro Tyr Ala Arg Asp Arg Val Val Glu Cys
                260                 265                 270

Tyr Phe Trp Ala Leu Gly Val Tyr Phe Glu Pro Gln Tyr Ser Gln Ala
        275                 280                 285

Arg Val Met Leu Val Lys Thr Ile Ser Met Ile Ser Ile Val Asp Asp
    290                 295                 300

Thr Phe Asp Ala Tyr Gly Thr Val Lys Glu Leu Glu Ala Tyr Thr Asp
305                 310                 315                 320

Ala Ile Gln Arg Trp Asp Ile Asn Glu Ile Asp Arg Leu Pro Asp Tyr
            325                 330                 335

Met Lys Ile Ser Tyr Lys Ala Ile Leu Asp Leu Tyr Lys Asp Tyr Glu
                340                 345                 350

Lys Glu Leu Ser Ser Ala Gly Arg Ser His Ile Val Cys His Ala Ile
        355                 360                 365

Glu Arg Met Lys Glu Val Val Arg Asn Tyr Asn Val Glu Ser Thr Trp
    370                 375                 380

Phe Ile Glu Gly Tyr Met Pro Pro Val Ser Glu Tyr Leu Ser Asn Ala
385                 390                 395                 400

Leu Ala Thr Thr Thr Tyr Tyr Leu Ala Thr Thr Ser Tyr Leu Gly
            405                 410                 415

Met Lys Ser Ala Thr Glu Gln Asp Phe Glu Trp Leu Ser Lys Asn Pro
                420                 425                 430

Lys Ile Leu Glu Ala Ser Val Ile Ile Cys Arg Val Ile Asp Asp Thr
        435                 440                 445

Ala Thr Tyr Glu Val Glu Lys Ser Arg Gly Gln Ile Ala Thr Gly Ile
    450                 455                 460

Glu Cys Cys Met Arg Asp Tyr Gly Ile Ser Thr Lys Glu Ala Met Ala
465                 470                 475                 480

Lys Phe Gln Asn Met Ala Glu Thr Ala Trp Lys Asp Ile Asn Glu Gly
            485                 490                 495

Leu Leu Arg Pro Thr Pro Val Ser Thr Glu Phe Leu Thr Pro Ile Leu
                500                 505                 510

Asn Leu Ala Arg Ile Val Glu Val Thr Tyr Ile His Asn Leu Asp Gly
        515                 520                 525

Tyr Thr His Pro Glu Lys Val Leu Lys Pro His Ile Ile Asn Leu Leu
    530                 535                 540

Val Asp Ser Ile Lys Ile
545                 550
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (iv) ANTI-SENSE: NO (xi) SEQUENCE DESCRIPTION: SEQ ID NO:9:

CGTTGGATCC CCACCTCATC CGAAATGAAC                                30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR."

(iii) HYPOTHETICAL: NO (iv) ANTI-SENSE: YES (xi) SEQUENCE DESCRIPTION: SEQ ID NO:10:

GGCTGAGCTC CTGGACGCAG AGATCAAACC                                30

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer for
            PCR (reverse)."

(iii) HYPOTHETICAL: NO (iv) ANTI-SENSE: YES (xi) SEQUENCE DESCRIPTION: SEQ ID NO:11:

GCCGGATCCT TATGACTAGT TGCACCACCA CGCAGCAAAC TG                      42

(2) INFORMATION FOR SEQ ID NO:12:

(i) SEQUENCE CHARACTERISTICS:
        (A) LENGTH: 593 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Phytophthora parasitica (ix) FEATURE:
        (A) NAME/KEY: CDS
        (B) LOCATION: 207..563

(xi) SEQUENCE DESCRIPTION: SEQ ID NO:12:

```
GTCGACGAAA GCCGAAGTGC GTGGCAGATC TTGCCGTTCG AATGCTACGC GCCACGGCAA      60

AACCTACACG GTACAACAGC TTCAAATAAA CCTGCAAGCG AGCCGCCAGC CCAACTCCAG     120

CTAGTCAAGC CTAGTTTGCC TCCAACTGCC ATTGTGCAAT TTGCTCTCAT CCACACCCAC     180

CCCACTTCTC CCCCACCTCA TCCGAA ATG AAC TTC CGC GCT CTG TTC GCC GCC     233
                             Met Asn Phe Arg Ala Leu Phe Ala Ala
                              555                 560

ACC GTC GCC GCC CTC GTC GGC TCC ACC TCC GCC ACC ACG TGC ACC ACC     281
Thr Val Ala Ala Leu Val Gly Ser Thr Ser Ala Thr Thr Cys Thr Thr
            565                 570                 575

ACG CAG CAA ACT GCG GCG TAC GTG GCG CTC GTA AGC ATC CTC TCG GAC     329
Thr Gln Gln Thr Ala Ala Tyr Val Ala Leu Val Ser Ile Leu Ser Asp
        580                 585                 590

ACG TCG TTC AAC CAG TGC TCG ACG GAC TCT GGC TAC TCA ATG CTG ACG     377
Thr Ser Phe Asn Gln Cys Ser Thr Asp Ser Gly Tyr Ser Met Leu Thr
    595                 600                 605

GCC ACC TCG TTG CCC ACG ACG GAG CAG TAC AAG CTC ATG TGC GCG TCG     425
Ala Thr Ser Leu Pro Thr Thr Glu Gln Tyr Lys Leu Met Cys Ala Ser
610                 615                 620

ACG GCG TGC AAG ACG ATG ATC AAC AAG ATC GTG ACG CTG AAC CCG CCC     473
Thr Ala Cys Lys Thr Met Ile Asn Lys Ile Val Thr Leu Asn Pro Pro
625                 630                 635                 640

GAC TGC GAG TTG ACG GTG CCT ACG AGC GGC CTG GTA CTC AAC GTG TTC     521
Asp Cys Glu Leu Thr Val Pro Thr Ser Gly Leu Val Leu Asn Val Phe
                645                 650                 655

ACG TAC GCG AAC GGG TTC TCG TCT ACG TGC GCG TCA CTG TAA             563
Thr Tyr Ala Asn Gly Phe Ser Ser Thr Cys Ala Ser Leu
            660                 665

GCGGGTTTGA TCTCTGCGTC CAGAATCGAT                                     593
```

(2) INFORMATION FOR SEQ ID NO:13:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:13:

```
Met Asn Phe Arg Ala Leu Phe Ala Ala Thr Val Ala Ala Leu Val Gly
  1               5                  10                  15

Ser Thr Ser Ala Thr Thr Cys Thr Thr Thr Gln Gln Thr Ala Ala Tyr
             20                  25                  30

Val Ala Leu Val Ser Ile Leu Ser Asp Thr Ser Phe Asn Gln Cys Ser
         35                  40                  45

Thr Asp Ser Gly Tyr Ser Met Leu Thr Ala Thr Ser Leu Pro Thr Thr
     50                  55                  60

Glu Gln Tyr Lys Leu Met Cys Ala Ser Thr Ala Cys Lys Thr Met Ile
 65                  70                  75                  80

Asn Lys Ile Val Thr Leu Asn Pro Pro Asp Cys Glu Leu Thr Val Pro
                 85                  90                  95

Thr Ser Gly Leu Val Leu Asn Val Phe Thr Tyr Ala Asn Gly Phe Ser
            100                 105                 110
```

```
Ser Thr Cys Ala Ser Leu
      115

(2) INFORMATION FOR SEQ ID NO:14:

(i) SEQUENCE CHARACTERISTICS:
        (A) LENGTH: 1368 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:14:

AAGCTTTACG AATTAGATGT AAAAAGACAC AAACTACTTA TATATATTAC CAAAGTAACT        60

TGAAAGTTTA AAATTTCAAT TAGAACTATA GTAGGGTAAA ACTGTCTATT TAAAATCAGT       120

ATTTAAAAAG GCATGAGCGA AAGATGAGGC GTTTTATCTA ACACGAAGCG AGGTGTAAGC       180

CCCATGGTGT TTTATTTTTA TATTTTATAA ATTTATAAAA TCATTATATA AATCAGAAAA       240

ATACACTAAA ATTGTGAAAA GTTAAAGAAA ATTATAGAAT TAATATATAT ATATATATAT       300

ATATATATAT ATATATATAT ATATATATAT ATATATATAA ATGTATGTGT GTGTGTGTGT       360

GTATCGCATG CGCGCGACCA TGCAACTTTT TTTTCTTGAA AAAATAAAAG GCGTAAAGAT       420

ACATTATACC TATGTCATCA AAACAATATA ATATATATAT ATATATATAT ATATATATAT       480

ATATATATAA ATGTATGTGT GTGTGTGTGT GTATCGCATG CGCGCGACCA TGCAACTTTT       540

TTTTCTTGAA AAAATAAAAG GCGTAAAGAT ACATTATACC TATGTCATCA AAACAATATA       600

AAAACTAGAG CGATACCAAA GGAAATTTTA AATTCAAAAA CTAACTTGAA ATTAATATAT       660

TTAAAATTTC ATTTTTTTTT GTGTGGAGAA AACAAAGCAT AACACTTTGC TTTGTAACAC       720

TTTGCCTAGG TGAATGTCAG GGCTTATGCT CCACGATACT TATGCCCTGC CAGTACACCT       780

CGCAGTGGGA CTCGCTGAAA AAACGTCTTT GTTGTGAGAA ATTGCAATTT TGAACCTCTA       840

CAATTTCGAC AAAACCTTGG TTCGTGAAAA CTGTTTGATT AACTTTTAGA CCATCCAGTC       900

AATTTAACTC TAAACTGACC TAAATAAATA CTACGTACAC TAGTCTTTAA GTTCATCAAA       960

GTGGACTCTG CATTAATAAT TGAAATTTAT GCCGCAACAA TGACATTAGG TTTTATAAAT      1020

AAAGTAATAG GAATTTGATA GTTCCAGGAA ACAACTCTAC AGTACTCCCT TATTTTGTGC      1080

CTTTTTAAAT AATATTATTC AGTTGACGAA ACAAATAAAT AAAATATTTG GGAAACTGGA      1140

TCAATAGACC CCAGACGCCA ACAATGAATC AAAAGGCTGC TAGCTAGTGT AAAGTCTAGT      1200

AAGGCAACTG GGAAATTAAA TGATTAGGTG CTTTTGATCA ATTACATTAA CTAGTCTCTC      1260

ACCACTATAT ATACTTGTCC CTTCTCTTCC ATTTAAGTAG AGTTCCTTTC TTTCTTCCTT      1320

AAAACTTAAA AGAACAAGTA AAAATACACT CATCTTTAAT TAGCAATG                  1368
```